US008772012B2

(12) United States Patent
Katahira et al.

(10) Patent No.: US 8,772,012 B2
(45) Date of Patent: Jul. 8, 2014

(54) XYLOSE ISOMERASE AND USE THEREOF

(75) Inventors: Satoshi Katahira, Nagakute (JP); Kenro Tokuhiro, Nagakute (JP); Nobuhiko Muramoto, Nagakute (JP); Haruo Takahashi, Nagakute (JP); Yoshina Takahashi, legal representative, Ogaki (JP); Shigeharu Moriya, Wako (JP); Moriya Ohkuma, Wako (JP)

(73) Assignees: Kabushiki Kaisha Toyota Chuo Kenkyusho, Nagakute (JP); Riken, Wako-shi (JP)

( * ) Notice: Subject to any disclaimer, the term of this patent is extended or adjusted under 35 U.S.C. 154(b) by 0 days.

(21) Appl. No.: 13/518,251

(22) PCT Filed: Dec. 22, 2010

(86) PCT No.: PCT/JP2010/073210
§ 371 (c)(1),
(2), (4) Date: Oct. 3, 2012

(87) PCT Pub. No.: WO2011/078262
PCT Pub. Date: Jun. 30, 2011

(65) Prior Publication Data
US 2013/0095538 A1 Apr. 18, 2013

(30) Foreign Application Priority Data

Dec. 22, 2009 (JP) ................... 2009-291463
Dec. 22, 2010 (JP) ................... 2010-285538

(51) Int. Cl.
C12N 9/90 (2006.01)
C12N 15/00 (2006.01)
C12N 1/20 (2006.01)
C07H 21/04 (2006.01)

(52) U.S. Cl.
USPC ............ 435/233; 435/320.1; 435/252.3; 536/23.1

(58) Field of Classification Search
USPC ....... 435/183, 320.1, 6, 252.3, 233; 536/23.2
See application file for complete search history.

(56) References Cited

U.S. PATENT DOCUMENTS

| | | | |
|---|---|---|---|
| 6,475,768 | B1 | 11/2002 | Otero et al. |
| 2006/0234364 | A1 | 10/2006 | Rajgarhia et al. |
| 2008/0014620 | A1 | 1/2008 | Op Den Camp et al. |
| 2008/0261287 | A1 | 10/2008 | Winkler et al. |
| 2009/0311771 | A1 | 12/2009 | Boles et al. |
| 2010/0035306 | A1 | 2/2010 | Op Den Camp et al. |
| 2010/0221807 | A1 | 9/2010 | Moriya et al. |
| 2011/0244525 | A1 | 10/2011 | Ronnow et al. |
| 2011/0269180 | A1 | 11/2011 | Brat et al. |
| 2011/0287505 | A1 | 11/2011 | Rajgarhia et al. |
| 2011/0287506 | A1 | 11/2011 | Rajgarhia et al. |
| 2011/0318790 | A1 | 12/2011 | Teunissen et al. |
| 2012/0003701 | A1 | 1/2012 | Brevnova et al. |
| 2012/0064580 | A1 | 3/2012 | Scharf et al. |
| 2012/0064607 | A1 | 3/2012 | Op Den Camp et al. |
| 2012/0225451 | A1 | 9/2012 | Winkler et al. |

FOREIGN PATENT DOCUMENTS

| | | |
|---|---|---|
| CN | 101052706 A | 10/2007 |
| JP | A-7-31465 | 2/1995 |
| JP | A-11-253917 | 9/1999 |
| JP | A-2003-070475 | 3/2003 |
| JP | A-2005-514951 | 5/2005 |
| JP | A-2006-525029 | 11/2006 |
| JP | 506383 * | 3/2008 |
| JP | A-2008-506383 | 3/2008 |
| JP | A-2008-079564 | 4/2008 |
| JP | A-2010-178677 | 8/2010 |
| JP | A-2011-024500 | 2/2011 |
| WO | WO 96/24667 A1 | 8/1996 |
| WO | WO 03/062430 A1 | 7/2003 |
| WO | WO 2004/099381 A2 | 11/2004 |
| WO | WO 2006/009434 A1 | 1/2006 |
| WO | WO 2006/096130 A1 | 9/2006 |
| WO | WO 2008/108116 A1 | 9/2008 |
| WO | WO 2010/000464 A1 | 1/2010 |
| WO | WO 2010/005551 A2 | 1/2010 |
| WO | WO 2010/070549 A1 | 6/2010 |
| WO | WO 2010/074577 A1 | 7/2010 |
| WO | WO 2010/117843 A2 | 10/2010 |

OTHER PUBLICATIONS

Weinstock et al., Uniprot database, Accession No. C4G751, Jul. 2009.*
Brat et al., "Functional Expression of a Bacterial Xylose Isomerase in *Saccharomyces cerevisiae*," *Applied and Environmental Microbiology*, vol. 75, No. 8, pp. 2304-2311, Apr. 2009.
Walfridsson et al., "Ethanolic Fermentation of Xylose with *Saccharomyces cerevisiae* Harboring the *Thermus thermophilus* xylA Gene, Which Expresses an Active Xylose (Glucose) Isomerase," *Applied and Environmental Microbiology*, vol. 62, No. 12, pp. 4648-4651, Dec. 1996.
Ho et al., "Expression of the *E. coli* Xylose Isomerase Gene by a Yeast Promoter," *Biotechnology and Bioengineering Symposium*, No. 13, pp. 245-250, 1983.
Harhangi et al., "Xylose metabolism in the anaerobic fungus *Piromyces* sp. strain E2 follows the bacterial pathway," *Arch. Microbiol.*, vol. 180, No. 2, pp. 134-141, Jun. 13, 2003.
Hanes, "The Effect of Starch Concentration Upon the Velocity of Hydrolysis by the Amylase of Germinated Barley," *Biochemical Journal*, vol. 26, No. 5, pp. 1406-1421, Jul. 9, 1932.
Ozcan et al., "Function and Regulation of Yeast Hexose Transporters," *Microbiology and Molecular Biology Reviews*, vol. 63, No. 3, pp. 554-569, Sep. 1999.
Tartar et al., "Parallel metatranscriptome analyses of host and symbiont gene expression in the gut of the termite *Reticulitermes flavipes*," *Biotechnology for Biofuels*, vol. 2, No. 25, pp. 1-19, Oct. 15, 2009.

(Continued)

Primary Examiner — Maryam Monshipouri
(74) Attorney, Agent, or Firm — Oliff PLC

(57) ABSTRACT

It is an object of the disclosure of the present description to provide an eukaryotic cell having xylose utilization ability. The disclosure of the present description provides a novel eukaryotic cell having xylose utilization ability by transforming a yeast or other eukaryotic cell using DNA that codes a xylose isomerase from a termite protist.

19 Claims, 12 Drawing Sheets

(56) References Cited

OTHER PUBLICATIONS

Azuma et al., "Studies on Digestive System of Termites III. Digestibility of Xylan by Termite *Reticulitermes speratus* (Kolbe)," *Wood Research: Bulletin of the Wood Research Institute Kyoto University*, No. 79, pp. 41-51, 1993.

Weinstock et al., "hypothetical protein GCWU000182_03087 [Abiotrophia defective ATCC 49176]," Database GenBank [Online], Uploaded May 8, 2009.

Todaka et al., "Screening of cellulose genes from symbiotic protists of lower termites for the secretory expression in *Saccharomyces cerevisiae*," *Dai 61 Kai Abstracts of the Annual Meeting of the Society for Biotechnology*, p. 17, Aug. 25, 2009.

Matsushika et al., "Ethanol production from xylose in engineered *Saccharomyces cerevisiae* strains: current state and perspectives," *Appl. Microbiol. Biotechnol.*, vol. 84, No. 1, pp. 37-53, Jul. 2, 2009.

Karhumaa et al., "Investigation of limiting metabolic steps in the utilization of xylose by recombinant *Saccharomyces cerevisiae* using metabolic engineering," *Yeast*, vol. 22, No. 5, pp. 359-368, Apr. 15, 2005.

Madhavan et al., "Xylose isomerase from polycentric fungus *Orpinomyces*: gene sequencing, cloning, and expression in *Saccharomyces cerevisiae* for bioconversion of xylose to ethanol," *Appl. Microbiol. Biotechnol.*, vol. 82, No. 6, pp. 1067-1078, Dec. 3, 2008.

Chu et al., "Genetic improvement of *Saccharomyces cerevisiae* for xylose fermentation," *Biotechnology Advances*, vol. 25, No. 5, pp. 425-441, Apr. 24, 2007.

Moriya et al., "How to learn the biomass utilization systems from termite: The strategy of comprehensive approach," *Dai 61 Kai Abstracts of the Annual Meeting for the Society for Biotechnology*, pp. 201, Aug. 25, 2009, Japanese.

Ohkuma, "Termite symbiotic systems: efficient bio-recycling of lignocellulose," *Appl. Microbiol. Biotechnol.*, vol. 61, No. 1, pp. 1-9, Jan. 14, 2003.

Okuma et al., *Seibutsu no Kagaku Iden*, vol. 63, No. 4, pp. 110-113, Jul. 1, 2009, Japanese.

Okuma et al., "New Genome Approaches to Uncultured Microorganisms and Symbiosis in the Gut of Termites," *Bioindustry*, vol. 25, No. 12, pp. 81-88, Dec. 12, 2008, Japanese.

Feb. 1, 2012 International Preliminary Report on Patentability issued in Application No. PCT/JP2010/073210 (with translation).

Apr. 5, 2011 International Search Report issued in Application No. PCT/JP2010/073210 (with translation).

Mar. 28, 2011 Written Opinion of International Searching Authority issued in Application No. PCT/JP2010/073210 (with translation).

Gardonyi et al., "The *Streptomyces rubiginosus* xylose isomerase is misfolded when expressed in *Saccharomyces cerevisiae*," *Enzyme and Microbial Technology*, vol. 32, pp. 252-259, 2003.

May 6, 2013 Office Action issued in Chinese Patent Application No. 201080064297.8 (with translation).

\* cited by examiner

XYLOSE ISOMERASE AND USE THEREOF

TECHNICAL FIELD

The present application is a National Phase entry of PCT/JP2010/073210 filed on Dec. 22, 2010, which claims priority to Japanese Patent Application No. 2009-291463 filed on Dec. 22, 2009 and Japanese Patent Application No. 2010-285538 filed on Dec. 22, 2010. The entire contents of Japanese Patent Application No. 2009-291463 and Japanese Patent Application No. 2010-285538 are incorporated by reference into the present application.

BACKGROUND ART

In recent years, techniques are being studied for converting sustainable biomass into useful substances and using the same as an energy source or industrial raw material to replace petroleum resources. Ethanol and other useful substances produced by microbial fermentation using biomass as the raw material are promising as substitute raw materials from the standpoint of reducing petroleum consumption and controlling the increase of carbon dioxide in the atmosphere. Of the various kinds of biomass, herbaceous and woody plants and the like consisting primarily of lignocellulose may be useful as raw materials because they are not suitable as foodstuffs.

The principal sugars in lignocellulose are the glucose making up cellulose and the xylose making up hemicellulose. A saccharified composition containing primarily these simple sugars is obtained by chemical or enzymatic decomposition of lignocellulose. For the industrial manufacture of useful substances from lignocellulose, there is a need for microorganisms that efficiently utilize the sugars in such a saccharified composition and can ferment them productively and with high yield.

*Saccharomyces cerevisiae* and other yeasts with strong ethanol fermentation ability can generally utilize glucose, mannose and galactose, but not xylose. Thus, for efficient fermentation using lignocellulose as a raw material, these yeasts need to be modified to make them capable of utilizing xylose. The use of xylose isomerases (XI), isomerizing enzymes that convert xylose to xylulose, has been reported as a way for yeasts and the like to utilize xylose (Patent Literatures 1 and 2).

It has been reported that the activity of the following XI enzymes is sufficiently expressed in yeasts: XI from an anaerobic mold *Piromyces* sp. E2 (Patent Literature 1), XI from the anaerobic mold *Cyllamyces aberensi*, XI from the bacteria *Bacteroides thetaiotaomicron* (Patent Literature 2), and XI from the bacteria *Clostridium phytofermentans* (Non-patent Literature 1). XI genes from various organisms other than the above have also been introduced into yeasts, but have not been able to express their activity sufficiently (Non-patent Literatures 1, 2, 3 and 4). It has been found that xylose isomerases have common conserved regions (Non-patent Literature 5), and since XI enzymes that are actively expressed in yeasts and those that are not actively expressed all carry these conserved regions, the possession of a conserved region is not a sufficient condition for active expression of an XI in yeasts. The sequence characteristics necessary for active expression in yeasts are still entirely unknown.

There has also been very little research into the enzymological characteristics of xylose isomerases that function effectively in yeasts (Non-patent Literatures 1, 6 and 7).

Termites and other wood-degrading insects that use the woody component cellulose as an energy source break down cellulose with cellulose-degrading enzymes called cellulases. Cellulases from these insects are known to have extremely strong cellulose-degrading ability. The cellulases that act on cellulose in the termite gut are classified generally into two kinds: the termite's own cellulases and those belonging to symbiotic protists and other microorganisms in the termite's gut. Symbiotic protists living in the hindgut of lower termites play a principal role in cellulose decomposition, but these protists are difficult to culture, and past research has not advanced very far. At present, cellulases and genes from termite protists have been disclosed (Patent Literatures 3 and 4).

CITATION LIST

Patent Literature

Patent Literature 1: Japanese Translation of PCT Application No. 2005-514951
Patent Literature 2: Japanese Translation of PCT Application No. 2006-525029
Patent Literature 3: Japanese Patent Application Publication No. 2003-7047
Patent Literature 4: WO 2008/108116

Non Patent Literature

Non-patent Literature 1: Brat D, Boles E, Wiedemann B., Appl Environ Microbiol. 2009; 75(8): 2304-11
Non-patent Literature 2:
Gardonyi, M. and Hahn-Hagerdahl, B. (2003), Enzym. Microb. Technol. 32, 252-259.
Non-patent Literature 3: Walfridsson, M., Bao, X., Anderlund, M., Lilius, G., Bulow, L., Hahn-Hagerdal, B. (1996) Appl Environ Microbiol 62: 4648-51.
Non-patent Literature 4: Ho, N. W. Y., P. Stevis, S. Rosenfeld, J. J. Huang, and G. T. Tsao. (1983) Biotechnol. Bioeng. Symp. 13: 245-250.
Non-patent Literature 5: Harhangi, H. R., A. S. Akhmanova, R. Emmens, C. van der Drift, W. T. de Laat, J. P. van Dijken, M. S. Jetten, J. T. Pronk, and H. J. Op den Camp. 2003. Arch Microbiol 180: 134-41.
Non-patent Literature 6: Hanes, C. S., Biochemical Journal 1932; 26(5): 1406-1421.
Non-patent Literature 7: Ozcan, S., Johnston M., Microbiol Mol Biol Rev 1999; 63: 554-569.

SUMMARY OF INVENTION

However, no xylose isomerase of a termite protist has been discovered, nor have any been known. Even if a xylose isomerase from a termite protist were discovered, moreover, the amino acid sequence characteristics necessary for active expression in yeasts and the like are unknown as discussed above, and since the existence of conserved regions is not a guarantee of active expression, it would be extremely difficult to predict whether the original XI activity would be retained if the enzyme were to be expressed in a different species of microorganism such as a yeast. Moreover, the study of cellulases from termite protists has not made much progress because these organisms are difficult to culture, and compatibility with yeasts has been assumed to be low because termite protists are evolutionarily distant from yeasts.

It is an aim of the disclosures of this Description to provide a novel xylose isomerase that functions effectively in yeasts, as well as a use therefor.

Upon searching for xylose isomerases among the proteins of termite protists, which have been thought to have poor compatibility with yeasts, the inventors not only discovered a novel xylose isomerase, but discovered that this xylose isomerase is suited to expression in yeast cells when introduced into a yeast. The followings are provided by the disclosures of this Description.

The Disclosure of this Description provide a xylose isomerase that is any of the following:

(A) a protein that has an amino acid sequence represented by any of SEQ ID NOS: 2, 4, 6, 8, 10, 12 and 14;

(B) a protein that has an amino acid sequence represented by any of SEQ ID NOS: 2, 4, 6, 8, 10, 12 and 14 with one or more amino acids deleted, substituted or added therein, and having xylose isomerase activity;

(C) a protein that has an amino acid sequence having at least 70% identity with an amino acid sequence represented by any of SEQ ID NOS: 2, 4, 6, 8, 10, 12 and 14, and that has xylose isomerase activity;

(D) a protein that is coded by DNA hybridizing under stringent conditions with DNA complementary to DNA having a nucleotide sequence represented by any of SEQ ID NOS: 1, 3, 5, 7, 9, 11 and 13, and that has xylose isomerase activity;

(E) a protein that is coded by DNA having a nucleotide sequence having at least 70% identity with a nucleotide sequence represented by any of SEQ ID NOS: 1, 3, 5, 7, 9, 11 and 13, and that has xylose isomerase activity.

Said (A) through (E) may be as follows:

(A) a protein that has an amino acid sequence represented by any of SEQ ID NOS: 2, 4, 6 and 8;

(B) a protein having an amino acid sequence represented by any of SEQ ID NOS: 2, 4, 6 and 8 with one or more amino acids deleted, substituted or added therein, and that has xylose isomerase activity;

(C) a protein that has an amino acid sequence having at least 70% identity with an amino acid sequence represented by any of SEQ ID NOS: 2, 4, 6 and 8, and that has xylose isomerase activity;

(D) a protein that is coded by DNA hybridizing under stringent conditions with DNA complementary to DNA having a nucleotide sequence represented by any of SEQ ID NOS: 1, 3, 5 and 7, and that has xylose isomerase activity;

(E) a protein that is coded by DNA having a nucleotide sequence having at least 70% identity with a nucleotide sequence represented by any of SEQ ID NOS: 1, 3, 5 and 7, and that has xylose isomerase activity.

Said (A) through (E) may be as follows:

(A) a protein that has the amino acid sequence represented by SEQ ID NO:2;

(B) a protein that has the amino acid sequence represented by SEQ ID NO:2 with one or more amino acids deleted, substituted or added therein, and that has xylose isomerase activity;

(C) a protein that has an amino acid sequence having at least 70% identity with the amino acid sequence represented by SEQ ID NO:2, and that has xylose isomerase activity;

(D) a protein that is coded by DNA hybridizing under stringent conditions with DNA complementary to DNA having the nucleotide sequence represented by SEQ ID NO:1, and that has xylose isomerase activity;

(E) a protein that is coded by DNA having a nucleotide sequence having at least 70% identity with the nucleotide sequence represented by SEQ ID NO:1, and that has xylose isomerase activity.

The Disclosure of this Description may provide a DNA that is any of the following:

(a) DNA that has a nucleotide sequence represented by any of SEQ ID NOS: 1, 3, 5, 7, 9, 11 and 13;

(b) DNA that hybridizes under stringent conditions with DNA complementary to DNA having a nucleotide sequence represented by any of SEQ ID NOS: 1, 3, 5, 7, 9, 11 and 13, and that codes a protein having xylose isomerase activity;

(c) DNA that has a nucleotide sequence having at least 70% identity with a nucleotide sequence represented by any of SEQ ID NOS: 1, 3, 5, 7, 9, 11 and 13, and that codes a protein having xylose isomerase activity;

(d) DNA that codes a protein having an amino acid sequence represented by any of SEQ ID NOS: 2, 4, 6, 8, 10, 12 and 14;

(e) DNA that codes a protein having an amino acid sequence represented by any of SEQ ID NOS: 2, 4, 6, 8, 10, 12 and 14 with one or more amino acids deleted, substituted or added therein, and that has xylose isomerase activity;

(f) DNA that codes a protein that has an amino acid sequence having at least 70% identity with an amino acid sequence represented by any of SEQ ID NOS: 2, 4, 6, 8, 10, 12 and 14, and that has xylose isomerase activity.

Said (a) through (f) may be as follows:

(a) DNA that has a nucleotide sequence represented by any of SEQ ID NOS: 1, 3, 5 and 7;

(b) DNA that hybridizes under stringent conditions with DNA complementary to DNA having a nucleotide sequence represented by any of SEQ ID NOS: 1, 3, 5 and 7, and that codes a protein having xylose isomerase activity;

(c) DNA that has a nucleotide sequence having at least 70% identity with a nucleotide sequence represented by any of SEQ ID NOS: 1, 3, 5 and 7, and that codes a protein having xylose isomerase activity;

(d) DNA that codes a protein having an amino acid sequence represented by any of SEQ ID NOS: 2, 4, 6 and 8;

(e) DNA that codes a protein having an amino acid sequence represented by any of SEQ ID NOS: 2, 4, 6 and 8 with one or more amino acids deleted, substituted or added therein, and that has xylose isomerase activity;

(f) DNA that codes a protein having an amino acid sequence having at least 70% identity with an amino acid sequence represented by any of SEQ ID NOS: 2, 4, 6 and 8, and that has xylose isomerase activity.

Said (a) through (f) may be as follows: (a) DNA that has the nucleotide sequence represented by SEQ ID NO:1;

(b) DNA that hybridizes under stringent conditions with DNA complementary to DNA having the nucleotide sequence represented by SEQ ID NO:1, and that codes a protein having xylose isomerase activity;

(c) DNA that has a nucleotide sequence having at least 70% identity with the nucleotide sequence represented by SEQ ID NO:1, and that codes a protein having xylose isomerase activity;

(d) DNA that codes a protein having the amino acid sequence represented by SEQ ID NO:2;

(e) DNA that codes a protein having the amino acid sequence represented by SEQ ID NO:2 with one or more amino acids deleted, substituted or added therein, and that has xylose isomerase activity;

(f) DNA that codes a protein that has an amino acid sequence having at least 70% identity with the amino acid sequence represented by SEQ ID NO:2, and that has xylose isomerase activity.

The Disclosure of this Description may provide an eukaryotic cell that has been transformed with a DNA construct having any of the DNA as above, and that expresses a xylose isomerase. The eukaryotic cell may be a yeast. The yeast may belong to any genus selected from the group consisting of the *Saccharomyces, Kluyveromyces, Candida, Pichia, Schizosaccharomyces, Hancenula, Klocckera, Schwannio-*

*myces, Yarrowia* and *Issatchenkia*. The eukaryotic cell may secretorily produce a cellulase. The cell may produce one or two or more enzymes included in an enzyme group of an arabinose metabolic pathway. The eukaryotic cell may be provided with an exogenous or endogenous gene that produces any selected from a group consisting of ethanol, lactic acid, acetic acid, 1,3-propane-diole, propanol, butanol, succinic acid, ethylene, glycerol, farnesol, geranylgeraniol and squalene.

The Disclosure of this Description may provide an eukaryotic cell expression vector comprising any of the DNA.

The Disclosure of this Description may provide a method of preparing a transformed eukaryotic cell with imparted or improved xylose utilization properties. The method comprises a step of transforming an eukaryotic cell by introducing thereto any of the DNA.

The Disclosure of this Description may provide a method for producing a useful substance. The method comprising a step of culturing the eukaryotic any of the cell in the presence of xylose. The useful substance may be any selected from a group consisting of ethanol, lactic acid, acetic acid, 1,3-propane-diole, propanol, butanol, succinic acid, ethylene, glycerol, farnesol, geranylgeraniol and squalene.

DESCRIPTION OF EMBODIMENTS

The disclosures of the present teaching relate to the DNA of any of (a) through (f) above, and to a use therefor. The DNA of (a) above derives from an intestinal protist of a termite in all cases. The nucleotide sequences represented by SEQ ID NOS: 1, 3, 5 and 7 derive from an intestinal protist of *Reticulitermes speratus*, while the nucleotide sequences represented by SEQ ID NOS: 9, 11 and 13 derive from an intestinal protist of *Mastotermes darwiniensis*. DNA having these nucleotide sequences encodes a xylose isomerase in all cases. The amino acid sequences encoded by the nucleotide sequences represented by SEQ ID NOS: 1, 3, 5 and 7 had 51%, 50%, 52% and 52% identity, respectively, with the amino acid sequence encoded by the *Piromyces* sp. E2 xylose isomerase gene disclosed in Patent Literature 1. Meanwhile, the identity between the amino acid sequences coded by the nucleotide sequences represented by SEQ ID NOS: 9, 11 and 13 and the amino acid sequence coded by the *Piromyces* sp. E2 xylose isomerase gene disclosed in Patent Literature 1 was 75%, 74% and 72%, respectively.

That is, DNA having these nucleotide sequences and the amino acids coded by this DNA differ greatly from conventional xylose isomerase gene sequences and amino acid sequences. Nonetheless, this DNA imparts xylose utilization ability to eukaryotic cells when it is introduced into yeasts and other eukaryotic cells.

Figure 1:
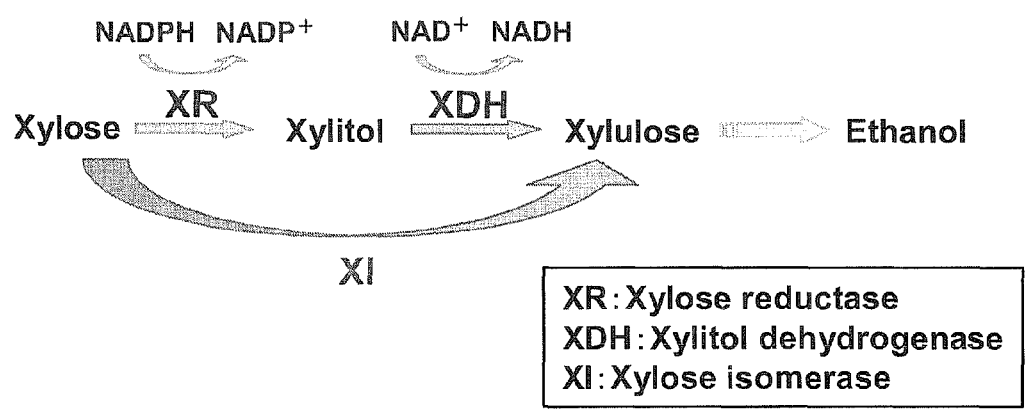
FIG. 1 shows an outline of xylose metabolic pathways.

A xylose metabolic pathway is necessary for yeasts and other eukaryotic cells to utilize xylose. As shown in FIG. 1, possible xylose metabolism pathways include a pathway using xylose reductase (XR) and xylitol dehydrogenase (XDH) (FIG. 1, top), and a pathway using xylose isomerase (XI) (FIG. 1, bottom). As shown in FIG. 1, the XI pathway is considered superior from the standpoint of product yield because it converts xylose into xylulose in one step without the need for a coenzyme. XI (xylose isomerase) activity was observed in an intracellular extract of a yeast having the novel XI gene of the present teaching introduced therein, confirming that the novel XI gene is expressed in yeast and other eukaryotic cells, and the resulting XI functions in the cells. Various embodiments of the present invention are discussed below.

(DNA Encoding Xylose Isomerase)

As disclosed in this Description, DNA having a nucleotide sequence represented by any of SEQ ID NOS: 1, 3, 5, 7, 9, 11 and 13 is DNA having a novel nucleotide sequence first discovered by the inventors in this case, and that codes a xylose isomerase.

In the disclosures of this Description, embodiments of DNA other than DNA having any nucleotide sequence selected from the specific nucleotide sequences given above may be used as long as it has XI activity. That is, DNA that has a specific relationship with any of these nucleotide sequences and encodes a protein having XI activity is acceptable. One example of such an embodiment is DNA that hybridizes under stringent conditions with DNA complementary to DNA having any of the nucleotide sequences represented by SEQ ID NOS: 1, 3, 5, 7, 9, 11 and 13, that that encodes a protein having XI activity.

"XI activity" is the activity of isomerizing xylose into xylulose. XI activity can be measured by known methods using the reduction in the amount of xylose as the substrate of this isomerization reaction, or the amount of xylulose produced by the reaction. "Having XI activity" simply means that there is XI activity. Preferably, this means that the XI activity is equivalent to or greater than that of a protein consisting of an amino acid sequence represented by SEQ ID NO: 2 or the like which is encoded by DNA having a nucleotide sequence represented by SEQ ID NO: 1 or the like on which the complement DNA to be hybridized is based. To confirm whether or not the XI activity is equivalent or greater, in the case of DNA that hybridizes with the complement chain of DNA having the nucleotide sequence represented by SEQ ID NO: 1 for example, the XI activity is preferably at least 70% or more preferably at least 80% or still more preferably at least 90% or most preferably at least 100% of the XI activity of the cell extract or protein when a protein having the amino acid sequence represented by SEQ ID NO: 2 is expressed in a yeast or other eukaryotic cell.

XI activity is preferably measured in an extract or other XI-containing fraction from yeast or other eukaryotic cells that have been transformed with such DNA so as to express the protein encoded by the DNA. With XI activity measured in such a way, it is possible to reliably provide DNA encoding XI that can be used favorably to impart xylose utilization activity to eukaryotic cells. The presence or absence of XI activity can be evaluated by evaluating whether eukaryotic cells transformed with the DNA proliferate in culture using only xylose as a carbon source.

Stringent condition refers to conditions, for example in which so-called specific hybrid is formed, a non-specific hybrid is not formed. For example, a condition such that complementary strand of the DNA having high identity such as at least 70% identical, preferably at least 80% identity, more preferably at least 85%, or still more preferably at least 90%, or most preferably at least 95% identity with the nucleotide sequence represented by any one of SEQ ID NOS: 1, 3, 5, 7, 9, 11 or 13 hybridizes with the DNA while the complementary strand of the DNA having the lower identity does not hybridize with the DNA is included. Typically, Na salt concentration is 15 to 750 mM, preferably 50 to 750 mM, more preferably 300 to 750 mM, temperature is 25 to 70° C., preferably 50 to 70° C., more preferably 55° to 65° C., and formamide concentration is 0 to 50%, preferably 20 to 50%, more preferably 35 to 45%. Further, stringent condition includes filter washing condition after hybridization which Na salt concentration is 15 to 600 mM, preferably 50 to 600 mM, more preferably 300 to 600 mM and temperature is 50 to 70° C., preferably 55 to 70° C., more preferably 60° to 65° C., typically.

In a further embodiment, another example is DNA having 70% or greater identity with an amino acid sequence represented by any of SEQ ID NOS: 1, 3, 5, 7, 9, 11, and 13, and encoding a protein having XI activity. That is, this may be DNA that has a nucleotide sequence having at least 70% or preferably at least 80% or more preferably at least 85% or still more preferably at least 90% or most preferably at least 95% identity with a nucleotide sequence represented by any of SEQ ID NOS: 1, 3, 5, 7, 9, 11 and 13, and that encodes a protein having XI activity.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as Similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol. Biol, 215: P403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

In a further embodiment, another example is DNA encoding a protein that comprises an amino acid sequence represented by SEQ ID NOS: 2, 4, 6, 8, 10, 12 or 14 with 1 or more amino acids deleted, replaced or added therein, and that has XI activity. Mutations in any of the amino acid sequences represented by SEQ ID NO: 2 and the like may be of only one kind (deletion, substitution or addition), or may be of two or more kinds. The total number of these mutations is not particularly limited, but is preferably 30 or fewer, or more preferably about 1 to 10. 1 to 5 mutations are still more desirable. Examples of these include DNA that codes a protein having such mutations in the amino acid sequence represented by SEQ ID NO: 2 or the amino acid sequence represented by SEQ ID NO: 10, and having XI activity.

Conservative substitutions are preferred as examples of amino acid substitutions, and specific examples include the following bracketed substitutions: (glycine, alanine), (valine, isoleucine, leucine), (aspartic acid, glutamic acid), (asparagine, glutamine), (serine, threonine), (lysine, arginine), (phenylalanine, tyrosine).

In a further example, this may be DNA encoding a protein that has an amino acid sequence having 70% or greater identity with an amino acid sequence represented by any of SEQ ID NOS: 2, 4, 6, 8, 10, 12 and 14, that that has XI activity. The degree of identity is preferably at least 80%, or more preferably at least 85%, or still more preferably at least 90%, or most at least preferably 95%. Of these, one example is DNA encoding a protein that has an amino acid sequence having at least 70% or preferably at least 80% or more preferably at least 85% or still more preferably at least 90% or most preferably 95% identity with the amino acid sequence represented by SEQ ID NO: 2, and that has XI activity. The amino acid sequence represented by SEQ ID NO: 4 and the amino acid sequence represented by SEQ ID NO: 6 have 87% and 91% identity, respectively, with the amino acid sequence represented by SEQ ID NO: 2. Another example is DNA that codes a protein that has at least 70% or preferably at least 80% or more preferably at least 85% or still more preferably at least 90% or most preferably at least 95% identity with the amino acid sequence represented by SEQ ID NO: 14, and that has XI activity. The amino acid sequence represented by SEQ ID NO; 10 and the amino acid sequence represented by SEQ ID NO: 12 have 85% and 86% identity, respectively, with the amino acid sequence represented by SEQ ID NO: 14.

A nucleotide sequence encoding the amino acid sequence represented by SEQ ID NO: 2 or the like or an amino acid sequence having a specific relationship with this amino acid sequence as discussed above may have at least one nucleotide replaced with another kind of nucleotide in the nucleotide sequence that codes a specific amino acid sequence in accordance with genetic code degeneracy without altering the amino acid sequence of the protein. Thus, the DNA disclosed in this Description encompasses DNA encoding a nucleotide sequence that has been altered by substitution based on genetic code degeneracy.

The DNA of these various embodiments can be obtained as nucleic acid fragments by PCR amplification using primers designed based on the sequence of SEQ ID NO: 1 and the like for example, and using DNA extracted from termite protists or the like or nucleic acids from various cDNA libraries or genome DNA libraries or the like as the template. It can also be obtained as nucleic acid fragments by hybridization using nucleic acids from these libraries and the like as the template, with a DNA fragment that is part of an XI gene as the probe. Alternatively, an XI gene can be synthesized as a nucleic acid fragment by chemical synthesis methods and various other nucleic acid sequence synthesis methods that are known in the technical field.

(Xylose Isomerase)

A novel xylose isomerase is provided by the disclosures of this Description. The xylose isomerase disclosed in this Description can assume the following forms.

(A) A protein having an amino acid sequence represented by any of SEQ ID NOS: 2, 4, 6, 8, 10, 12 and 14.

(B) A protein having an amino sequence represented by any of SEQ ID NOS: 2, 4, 6, 8, 10, 12 and 14 with one or more amino acids deleted, substituted or added therein, and having XI activity.

(C) A protein having an amino acid sequence that has at least 70% identity with an amino sequence represented by any of SEQ ID NOS: 2, 4, 6, 8 10, 12 and 14, and having XI activity.

(D) A protein encoded by DNA that hybridizes under stringent conditions with DNA complementary to DNA having a nucleotide sequence represented by any of SEQ ID NOS: 1, 3, 5, 7, 9, 11 and 13, and having XI activity.

(E) A protein encoded by DNA having a nucleotide sequence having at least 70% identity with a nucleotide sequence represented by any of SEQ ID NOS: 1, 3, 5, 7, 9, 11 and 13, and having XI activity.

One example of this is a protein that has an amino acid sequence having at least 70% or preferably at least 80% or more preferably at least 85% or still more preferably at least 90% or most preferably at least 95% identity with the amino acid sequence represented by SEQ ID NO: 2, and that has XI activity. Another example is a protein that has an amino acid sequence having at least 70% or preferably at least 80% or more preferably at least 85% or still more preferably at least 90% or most preferably at least 95% identity with the amino acid sequence represented by SEQ ID NO: 14, and that has XI activity.

Another example is a protein that has an amino acid sequence comprising the amino acid sequence represented by SEQ ID NO: 2 with one or more amino acids deleted, substituted or added therein, and that has XI activity. Yet another example is a protein that has an amino acid sequence comprising the amino acid sequence represented by SEQ ID NO: 14 with one or more amino acids deleted, substituted or added therein, and that has XI activity.

An amino acid substitution, deletion or addition in (B) above is preferably introduced into a region other than those areas, such as catalyst domains of the isomerase and substrate binding domains, that are vital to enzyme activity. Such domains can be easily determined by a person skilled in the art from an analysis of homology with known xylose isomerases and other isomerases.

The inventors estimate that the $K_m$ value of a xylose isomerase is about 30 mM or less. According to the examples discussed below, the value for RsXIC1 is about 13 mM, which is relatively small in comparison with the 40 mM of known PiXI, and it is thought that such a $K_m$ value enhances xylose utilization because it is suited to the intracellular xylose concentration of yeasts. The $K_m$ value is preferably 30 mM or less, or more preferably 25 mM or less, or still more preferably 20 mM or less, or most preferably 15 mM or less. The $K_m$ value can be measured by a known method, and calculated by a known calculation method such as that disclosed in Non-Patent Literature 6.

Amino acid substitutions, deletions or additions can be introduced by ordinary techniques, such as for example by using a site-specific mutagenesis method or the like as discussed above to modify the nucleotide sequence encoding the amino acid sequence.

The xylose isomerase disclosed in this Description is obtained by transforming an eukaryotic cell or other suitable host with a DNA construct comprising DNA encoding the xylose isomerase, culturing the transformed host cells by ordinary methods well known to those skilled in the art, and collecting the xylose isomerase disclosed in this Description from the cultured cells or medium. A soluble fraction can be obtained from the cultured cells by disrupting the cells and subjecting them to a centrifugation or other separation operation, and a polypeptide can then be obtained from this fraction. The xylose isomerase disclosed in this Description can be isolated by a combination of commonly used purification techniques. Such techniques include ammonium sulfate fractionation, organic solvent treatment, centrifugation, ultrafiltration, various forms of chromatography (such as gel filtration chromatography, ion exchange chromatography, affinity chromatography and hydrophobic interaction chromatography), high-performance liquid chromatography (HPLC), electrophoresis and the like.

(Transformant)

The transformant disclosed in this Description is an eukaryotic cell that has been transformed with a DNA construct comprising the aforementioned DNA.

(Host)

The host of the transformant disclosed in this Description is not particularly limited as long as it is an eukaryotic cell. From the standpoint of substance production and the like, it may be an *Aspergillus* or other mold or yeast. Examples of *Aspergillus* species include *Aspergillus aculeatus, Aspergillus orizae* and the like. Examples of yeasts include various known yeasts including *Saccharomyces cerevisiae* and other *Saccharomyces* yeasts, *Schizosaccharomyces pombe* and other *Schizosaccharomyces* yeasts, *Candida shehatae* and other *Candida* yeasts, *Pichia stipitis* and other *Pichia* yeasts, *Hansenula* yeasts, *Klocckera* yeasts, *Schwanniomyces* yeasts and *Yarrowia* yeasts, *Trichosporon* yeasts, *Brettanomyces* yeasts, *Pachysolen* yeasts, *Yamadazyma* yeasts, *Kluyveromyces marxianus, Kluyveromyces lactic* and other *Kluyveromyces* yeasts, *Issatchenkia orientalis* and other *Issatchenkia* yeasts and the like. Of these, a *Saccharomyces* yeast is preferred from the standpoint of industrial utility and the like. Of these, *Saccharomyces cerevisiae* is preferred.

The DNA disclosed in this Description is carried by the host in such a way that it can be expressed. That is, it may be linked under the control of a suitable promoter, and a terminator, enhancer, replication origin (ori), marker or the like may also be provided. The promoter may be inductive or constitutive. Examples of constitutive promoters in yeasts include the 3-phosphoglycerate kinase (PGK) promoter, glyceraldehyde-3-phosphate dehydrogenase (GAPDH) promoter, alcohol dehydrogenase 1 (ADH1) promoter, histidine nutritional function gene (HIS3) promoter, cytochrome bc1 complex (CYC1) promoter and hyperosmolarity responsive 7 gene (HOR7) promoter and modifications of these.

The transformant disclosed in this Description is transformed with a DNA construct so as to preferably express a xylose isomerase. That is, transformation with a DNA construct preferably imparts the ability to transform xylose into xylulose. By acquiring XI activity, it acquires the ability to growth and perform fermentation using xylose as a carbon source.

The DNA disclosed in this Description may be carried outside the chromosomes of the host cell, but is preferably carried on the chromosomes. Multiple copies are preferably present so as to impart strong xylose conversion ability.

The transformant disclosed in this Description may also be one that secretorily expresses a cellulase or hemicellulase either extracellularly or on the cell surface. Examples include endoglucanase, cellobiohydrolase, β-glucosidase and various other cellulases as well as hemicellulase and other biomass degrading enzymes. Expression of such proteins allows for effective utilization of sugars other than lignin derived from lignocellulose. The transformant disclosed in this Description may also be one that has been given genetic engineering modifications as necessary, such as introduction of an exogenous gene or disruption of an endogenous gene.

The transformant disclosed in this Description may also be one that expresses one or two or more enzymes belonging to an enzyme group for metabolizing arabinose. Examples include an enzyme group of the arabinose metabolic pathway in bacteria (WO 2006/096130 and WO 2009/011591), L-arabinose isomerase (EC 5.3.1.4), L-ribulokinase (EC 2.7.1.16) and L-ribulose-5-phosphate-4-epimerase (EC 5.1.3.4), an enzyme group of the arabinose metabolic pathway in mold (Japanese Translation of PCT Application No. 2004-532008), aldose reductase (EC 1.1.1.21), L-arabinotol-4-dehydrogenase (EC 5.1.3.4), L-xylulose reductase (EC 5.1.3.4) and D-xylulose reductase (EC 1.1.1. 9). Expression of these proteins provides a transformant capable of utilizing arabinose.

The transformant disclosed in this Description preferably has enhanced expression of one or two or more genes selected from a group consisting of a gene encoding an alcohol dehydrogenase, a gene encoding a phosphofructokinase, a gene encoding a glucokinase and a gene encoding a hexokinase. Enhanced expression of these genes is especially desirable in yeasts. The alcohol dehydrogenase gene may also be an alcohol dehydrogenase-1 gene, the phosphofructokinase gene may be a phosphofructokinase-2 gene, the glucokinase gene may be a glucokinase-1 gene, and the hexokinase gene may be a hexokinase-2 gene. These enzymes all belong to the glycolytic system. Enhancing expression of genes that codes these enzymes serves to increase the production and/or activity of these enzymes, resulting in a yeast or other eukaryotic cell having a high level of such enzyme activity. By enhancing expression of these genes, it is possible to provide a yeast or other eukaryotic cell transformant with enhanced ability to utilize sugar raw materials having xylose and other non-fermenting sugars or a mixture of such sugars, and with strong fermentation ability.

A gene encoding such an enzyme may be either endogenous or exogenous in the yeast or other eukaryotic cell. Known genes encoding these enzymes may be used appropriately. Any gene capable of enhancing the glycolytic system may be used, without regard for origin. That is, the gene may derive from a yeast belonging to a species other than the host yeast or a yeast belong to another genus, or may derive from an organism other than a yeast, such as an animal, plant, fungus (mold or the like), bacteria or the like. A person skilled in the art can obtain information about such genes by accessing the NCBI (National Center for Biotechnology Information; www.ncbi.nlm.nih.gov) and other HPs. For example, the nucleotide sequences and amino acid sequences of the S. cerevisiae HXK1 gene (Accession No: NC_001138 or D50617), GLK1 gene (Accession No: NC_001135 or M24077), PFK2 gene (Accession No: NC_001145 or Z48755) and ADH1 gene (Accession No: NC_001147 or Z74828) can be obtained from the NCBI and the S. cerevisiae genome database (SGD: www.yeastgenome.org). A gene may consist of genome DNA or cDNA or the like.

When used in the present invention, these genes may also be genes encoding proteins having a specific relationship with the sequence information disclosed in the databases and the like, as long as they have the appropriate enzyme activity. In one such embodiment, a gene codes a protein having a published amino acid sequence with one or more amino acids deleted, substituted or added therein, and having enzyme activity to be enhanced in the present invention. Amino acid mutations to a disclosed amino acid sequence may be of one kind (deletions, substitutions or additions), or a combination of two or more kinds. The total number of such mutations is not particularly limited, but is preferably about 30 or less or more preferably about 1 to 10 or still more preferably 1 to 5. Conservative substitutions are preferred as amino acid substitutions.

In another embodiment, the gene used in the present teaching may be a gene encoding a protein that has an amino acid sequence having 70% or greater identity with a published amino acid sequence, and that has enzyme activity targeted for enhancement. The degree of identity is preferably at least 80%, or more preferably at least 85%, or still more preferably at least 90%, or most preferably at least 95%.

Enhanced expression of a gene (Xylu-PPP gene) encoding an enzyme selected from a group of enzymes (Xylu-PPP utilization enzyme group) that constitute a pathway for metabolizing xylose as part of the non-oxidative phase of the pentose phosphate pathway (PPP) is desirable for imparting xylose utilization ability to yeasts. The Xylu-PPP utilization enzyme group includes a series of enzymes involved in the pathway leading from xylose to glyceraldehyde-3-phosphate and fructose-6-phosphate, which are the final compounds of the pentose phosphate pathway. Included in this enzyme group are xylulokinase, ribulose 5-phosphate epimerase, ribose 5-phosphate isomerase, transaldolase and transketolase. A Xylu-PPP gene may be a gene encoding one of these, and one such gene or a combination of two or more may be used. A combination of three or more is preferred, and a combination of four is more preferred, and a combination of all (five enzymes) is most preferred.

Of the Xylu-PPP genes, xylulose kinase (XK) genes are carried by many microorganisms that utilize xylulose, including bacteria and yeasts. Any XK gene can be used without any particular limitations as to origin. Information about XK genes can be obtained as necessary by searching the HP of NCBI or the like. Preferred examples of XK genes include those derived from yeasts, lactobacilli, E. coli or plants. An example of an XK gene is XKS1 (GenBank: Z72979)(amino acid sequence and nucleotide sequence of CDS coding region), an XK gene from S. cerevisiae S288C.

Transaldolase (TAL) genes, transketolase (TAK) genes, ribulose 5-phosphate epimerase (RPE) genes and ribose 5-phosphate ketoisomerase (RKI) genes are carried by many organisms having pentose phosphate pathways. For example, S. cerevisiae and other commonly used yeasts also carry these genes. These genes can be used without any particular limitations as to source organism. Information about these genes can be obtained as necessary by accessing the HP of NCBI or the like. Preferable examples are various genes from eukaryotic cells or yeast or other cells in the same genus as the host cells, or more preferably from the same species as the host cells. A TAL1 gene can preferably be used as a TAL gene, a TKL1 gene and TKL2 gene as TKL genes, a RPE1 gene as a RPE gene and a RKI1 gene as a RKI gene. For example, a TAL1 gene from S. cerevisiae S288 (GenBank: U19102) (amino acid sequence and nucleotide sequence (complement chain) of CDS coding region), a TKL1 gene from S. cerevisiae S288 (GenBank: X73224) (amino acid sequence and nucleotide sequence of CDS coding region), an RPE1 gene from *S. cerevisiae* S288C (GenBank: X83571) (amino acid sequence and nucleotide sequence of CDS coding region), and an RKI1 gene from *S. cerevisiae* S288C (GenBank: Z75003) (amino acid sequence and nucleotide sequence (complement chain) of CDS coding region) are examples of these genes.

The transformant disclosed in this Description may be one capable of producing a desired useful substance by fermentation as explained below. An eukaryotic cell capable of producing a useful substance may be provided with an endogenous gene and/or exogenous gene involved in producing the useful substance. A desired endogenous gene may also be disrupted. Yeasts ordinarily produce ethanol by anaerobic fermentation, but a host that has been transformed by genetic engineering modifications or the like to make it capable of producing another useful substance is also possible. Examples of useful substances include not only ethanol but also lactic acid, acetic acid, 1,3-propane-diole, propanol, butanol, succinic acid, ethylene and glycerol. Preferably the transformant is capable of producing one or two or more of these as useful substances. The host of the transformant disclosed in this Description may comprise a genetic modification or the like to a yeast or the like that produces an organic acid such as lactic acid (Japanese Patent Application Publication No. 2003-259878, Japanese Patent Application Publication No. 2006-006271, Japanese Patent Application Publication No. 2006-20602, Japanese Patent Application Publication No. 2006-75133, Japanese Patent Application Publication No. 2006-2966377 and Japanese Patent Application Publication No. 2007-89466).

(Preparation of Transformant)

To obtain the transformant disclosed in this Description, a host cell is transformed with a recombinant vector or other DNA construct carrying the DNA disclosed in this Description in an expressable form. The DNA construct can typically take various forms as a recombinant vector for expressing the xylose isomerase coded by the DNA disclosed in this Description.

The DNA construct can be produced through integrating DNA fragment for gene recombination of the above gene of interest into the downstream of an appropriate promoter in an appropriate expression vector. As for promoters, beside the above, inducible promoters such as GAL promoter are included. In addition, the recombinant vector can include one or more element selected from the group consisting of a terminator, an enhancer, a replication origin (ori) and a marker, if needed. Further, if the recombinant vector is directed to integration of the DNA fragment to a chromosome such as gene replacement and gene knockout, the vector can include one or more homologous region with a predetermined area of the chromosome. The homologous region can be appropriately selected depending on the area. One or more materials of the DNA construct can be selected and used appropriately among yeast expression vectors commercially available.

Common operations needed for the preparation of above-described recombinant vector and the treatment of yeast as a recombinant host cell are usually carried out by those skilled in the art. Those skilled in the art can carry out these operations by referring experiment protocols described in, for example, Molecular Cloning, A Laboratory Manual (T. Maniatis, and J. Sambrook et al., Cold Spring Harbor Laboratory, 1982, 1989, 2001).

Introducing methods of the DNA construct into the host cell include calcium phosphate method, transformation, transfection, conjugation, protoplast fusion, electroporation, lipofection, lithium acetate method and any other methods known to the art. These techniques are described in published books including the above mentioned text. The transformant of the present Description can be obtained by screening by the marker gene or the expression of the activity of the gene among yeast which the vector is introduced.

(Method of Producing Useful Substance)

The useful substance production method disclosed in this Description is provided with a step of culturing the transformant disclosed in this Description in the presence of xylose. Because the transformant disclosed in this Description has xylose utilization ability, it can effectively use any xylose contained as a carbon source, and convert it into a useful substance in the production method disclosed in this Description. Thus, even when the medium contains saccharides of lignocellulose including xylose, this biomass carbon source can be effectively utilized and converted into a useful substance. In addition to xylose, the lignocellulose saccharides may include glucose, as well as hemicellulose decomposition products.

Xylose includes arabinoxylan, glucuronoxylan and other xylans. In nature, these polymers form one component of hemicellulose, and are present in lignocellulose and other forms of biomass and the like. Xylose can be obtained by digesting xylans with an endoxylanase, xylosidase or the like.

The useful substance may also be a compound that is not an intrinsic metabolite, but one that that the yeast has been made capable of synthesizing by a genetically engineered substitution, addition or the like in one or two or more enzymes in the glucose metabolism system. Examples of useful substances include ethanol as well as lower alcohols, lactic acid, acetic acid and other organic acids. In addition, 1,3-propane-diol, propanol, butanol, succinic acid, glycerol and ethylene, farnesol, geranylgeraniol, squalene and other terpenoids and fine chemicals (coenzyme Q10, vitamins and other raw materials and the like) obtained by addition of isoprenoid synthesis pathways. Further, glycerin, plastics, synthetic raw materials and the like obtained by modifications in the glycolytic system and other materials used in biorefinery technology are included. As an yeast has high performance of alcohol fermentation, the transformant can produce ethanol effectively in the medium with carbon source including xylose. An yeast having high performance of alcohol fermentation has high performance of an organic acid and other useful substances by modifications in the glycolytic system.

In the step of culturing, a medium which contains xylose as a carbon source is used. Further, the medium can contain glucose. Preferably, the carbon sources which are derived from biomass carbon source including lignocellulose. In addition, when yeast expresses cellulases and has an ability to metabolize cellulose, cellulose or the partial degradation products thereof can be included in the medium.

The culturing step can be accomplished according to a culture condition selected appropriately from the general culture conditions applied to the host cell of the transformant. Typically, static culture, shaking culture or aerated stirred culture or the like can be used as the culture for fermentation. The aeration conditions can be set appropriately as anaerobic conditions, microaerobic conditions or aerobic conditions. The culture temperature is not particularly limited, and can be in the range of 25° C. to 55° C. The culture time can be set as necessary, and can be a few hours to about 150 hours. The pH can be adjusted with an inorganic or organic acid or alkali solution or the like. An antibiotic such as ampicillin or tetracycline can be added to the medium as necessary during culture.

By means of the culturing step, a useful substance is produced according to the useful substance production ability of the microorganism used. For example, ethanol is obtained with the transformant that has the ability to produce ethanol. The transformant that has the ability to produce lactic acid and other organic acids due to biogenetic modification or the like can be used to produce lactic acid and the like. After completion of the useful substance production step, there can be a step in which the fraction containing the useful substance is collected from the culture liquid, and another step in which it is purified or concentrated. The processes for collection, purification and other process can be selected appropriately according to the type of useful substance and the like.

In addition, the culturing step can be accomplished according to the culture condition applied generally to yeast. Typically, static culture, shaking culture or aerated stirred culture or the like can be used as the culture for fermentation. The aeration conditions can be set appropriately as anaerobic conditions, microaerobic conditions or aerobic conditions. The culture temperature is not particularly limited, and can be in the range of 25° C. to 55° C. The culture time can be set as necessary, and can be a few hours to about 150 hours. The pH can be adjusted with an inorganic or organic acid or alkali solution or the like. An antibiotic such as ampicillin or tetracycline can be added to the medium as necessary during culture.

The useful substance production step may be followed by a step of collecting a useful substance-containing fraction from the culture liquid, and a further step of refining or concentrating this fraction. The collection step and refining or other step can be selected appropriately according to the type of useful substance and the like.

According to the above embodiment, the disclosure of this Description provides followings.

1. A DNA coding for a protein that has an amino acid sequence having at least 70%, preferably 80%, more preferably 85%, further more preferably 90%, still further preferably 95% identity with an amino acid sequence represented by SEQ ID NO: 14, and that has xylose isomerase activity.
2. A protein that has an amino acid sequence having at least 70%, preferably 80%, more preferably 85%, further more preferably 90%, still further preferably 95% identity with an amino acid sequence represented by SEQ ID NO: 14, and that has xylose isomerase activity.
3. A protein that has an amino acid sequence represented by any of SEQ ID NO: 2, with one or more amino acids deleted, substituted or added therein, and having xylose isomerase activity.
4. A protein that has an amino acid sequence represented by any of SEQ ID NO: 14, with one or more amino acids deleted, substituted or added therein, and having xylose isomerase activity.
5. A DNA comprising a nucleotide sequence represented by SEQ ID NO: 45.
6. A DNA comprising a nucleotide sequence represented by SEQ ID NO: 46.
7. A DNA comprising a nucleotide sequence represented by SEQ ID NO: 47.

EXAMPLES

The present teaching is explained in detail below using examples, but the present invention is not limited by these examples. The genetic recombination operations described below were performed in accordance with Molecular Cloning: A Laboratory Manual (T. Maniatis, et al., Cold Spring Harbor Laboratory).

Example 1

Obtaining Genes from *Reticulitermes speratus* Intestinal Protist cDNA Library

Figure 2:
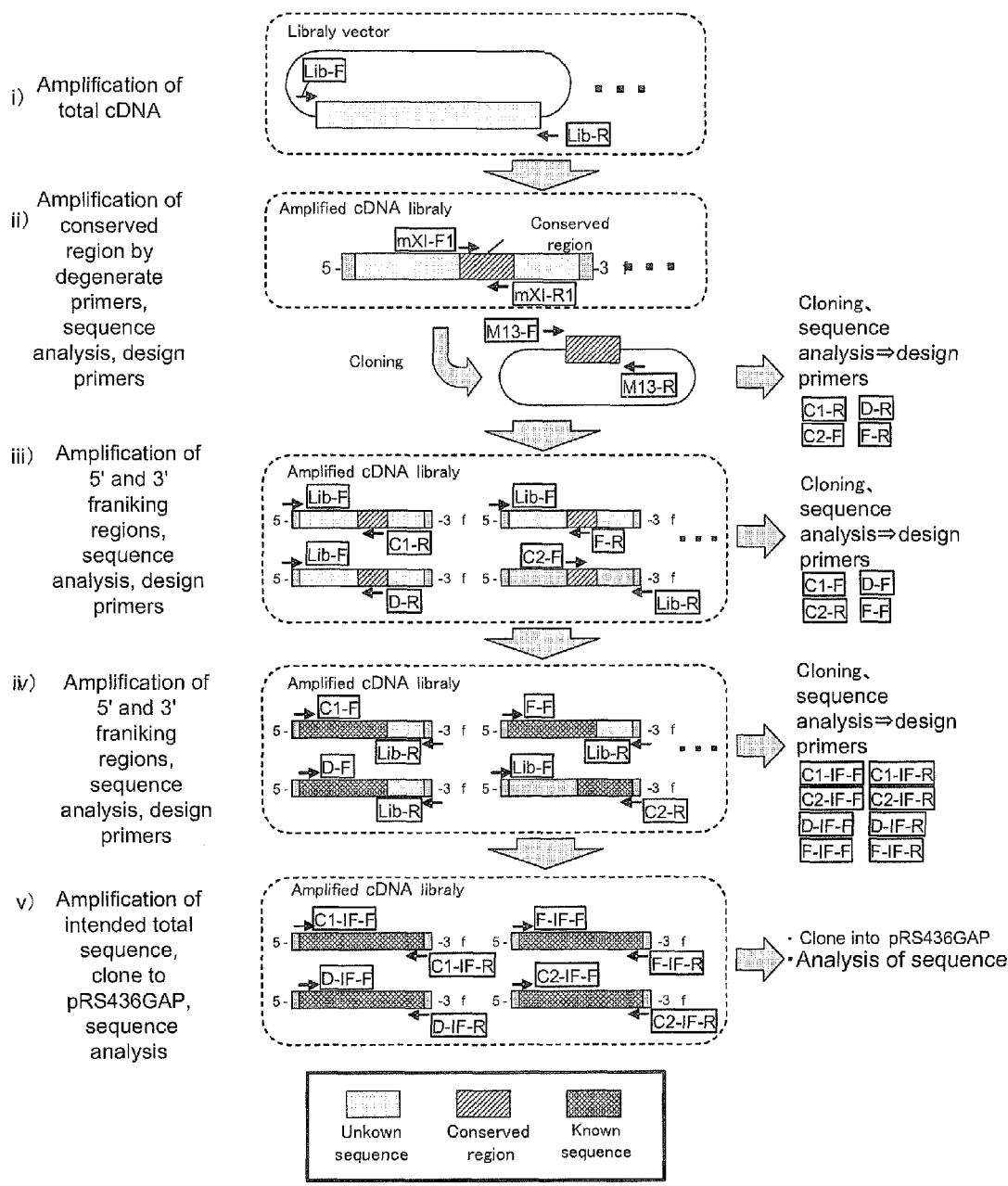
FIG. 2 shows procedures for obtaining xylose isomerase genes from a *Reticulitermes speratus* cDNA library.

Xylose isomerase-like genes were obtained from a *Reticulitermes speratus* intestinal protist metagenomic cDNA library. FIG. 2 shows the experimental procedures. Procedures i) through vi) in FIG. 2 are explained in sequence below.

i) Using the *Reticulitermes speratus* intestinal protist metagenomic cDNA library described in Japanese Patent Application No. 2007-053122 as a template, full-length cDNA inserted into a library vector using primers Lib-F and Lib-R was amplified by PCR to prepare an amplified cDNA library. The PCR reaction was performed under conditions of [98° C. 10 sec, 55° C. 15 sec, 72° C. 2 min]×30 cycles using PrimeSTAR HS DNA Polymerase (Takara Bio). The primers are shown below.

```
Lib-F:
                                        (SEQ ID NO: 15)
5'-taaacacacataaacaaacaaacccctcgagttaattaaattaat ccccc-3'

Lib-R:
                                        (SEQ ID NO: 16)
5'-ttactcctcgagggccacataggccgagctcttttttttttttt tt-3'
``` ii) Using the resulting PCR product as a template, PCR was performed using the degenerate primers mXI-F1 and mXI-R1, which amplify the conserved regions of xylose isomerases. The following PCR reaction was performed under conditions of [98° C. 10 sec, 55° C. 30 sec, 72° C. 1 min]×30 cycles using ExTaq HS DNA Polymerase (Takara Bio). The sequences of the primers are shown below.

```
mXI-F1:
                                        (SEQ ID NO: 17)
5'-tggggnggnmgngargntay-3' mXI-R1:
                                        (SEQ ID NO: 18)
5'-nggraaytgrtcngtrtccca-3'
```

In the degenerate primers, n represents a or t or g or c, m represents a or c, r represents a or g, and y represents c or t. The resulting 0.4 kbp DNA fragment was cloned into a pCR 2.1-TOPO vector using TOPO-TA Cloning Kit (Invitrogen). Using the resulting plasmid containing the 0.4 kbp DNA sequence as a template, the sequence of the DNA fragment inserted into the vector was analyzed with the primers M13-F and M13-R. The sequences of the primers are shown below.

```
M13-F:
                                        (SEQ ID NO: 19)
5'-gtaaaacgacggccagt-3'

M13-R:
                                        (SEQ ID NO: 20)
5'-caggaaacagctatgaccat-3'
```

Multiple novel sequences having high homology with conserved regions of xylose isomerases were obtained as a result of analysis. Four kinds of primers were also prepared based on the new sequence information. The sequences of the prepared primers are shown below.

```
C1-R:
                                            (SEQ ID NO: 21)
5'-tcgcttcaatattcagtttgaaatc-3'

C2-F:
                                            (SEQ ID NO: 22)
5'-atcatgcaactttggctggtcatac-3'

D1-R:
                                            (SEQ ID NO: 23)
5'-tcgcttcaatattcagtttaaaatc-3'

F-R:
                                            (SEQ ID NO: 24)
5'-accaatactccgaccataagtaacagctagtttc-3'
``` iii) Using primer sets comprising each of the primers C1-R, D1-R and F-R described in ii) together with the primer Lib-F described in i) and a primer set comprising the primer C2-F described in ii) together with the primer Lib-R described in i), PCR was performed using the amplified cDNA library described in i) as the template, amplifying the 5' flanking regions and 3' flanking regions, respectively. Roughly 0.9 kbp DNA fragments (C1-R, D1-R and F-R) corresponding to the resulting 5' flanking regions and a roughly 0.6 kbp DNA fragment (C2-F) corresponding to the 3' flanking region were cloned into a pCR 2.1-TOPO vector using a TOPO-TA Cloning Kit, and the sequence of the DNA fragment inserted into the vector was analyzed using the primers M13-F and M13-R. A primer comprising the 5' initiation codon and a primer comprising the 3' termination codon were prepared based on the resulting sequence information for the 5' flanking region and 3' flanking region. The sequences of the prepared primers are shown below.

```
C1-F:
                                            (SEQ ID NO: 25)
5'-ataaacaaacaaaccgcggaaaatgagtcagatattcaaagatat tcctgtgatcaaatatgaaggtcctgc-3'

C2-R:
                                            (SEQ ID NO: 26)
5'-tgatgcggccctcgagctactgaaacaaaatctggttaaatatac tctcaagaaactcttgacggc-3'

D1 -F:
                                            (SEQ ID NO: 27)
5'-ataaacaaacaaaccgcggaaaatgagtcaggaaatattcaaaaa cattccccaaatcaaatatgagggtcc-3'

F-F:
                                            (SEQ ID NO: 28)
5'-actcttgctggccacacatttc-3'
``` iv) Using primers sets comprising each of the primers C 1-F, D1-F and F-F described in iii) together with the primer Lib-R described in i) and a primer set comprising the primer C2-R described in iii) together with the primer Lib-F described in i), PCR was performed with the amplified cDNA library described in i) as the template, amplifying the 5' flanking region and 3' flanking region, respectively. The resulting roughly 1.4 kbp DNA fragment was cloned into a pCR 2.1-TOPO vector using a TOPO-TA Cloning Kit, and the sequence of the DNA fragment inserted into the vector was analyzed using primers M13-F and M13-R. Primers for obtaining full-length sequences from the initiation codon to the termination codon were prepared based on the sequences of the 5' and 3' flanking regions obtained as thus explained. The sequences are shown below.

```
C1-IF-F:
                                            (SEQ ID NO: 29)
5'-ataaacaaacaaaccgcggaaaatgagtcagatattcaaagatat tcctgtg-3'

C1-IF-R:
                                            (SEQ ID NO: 30)
5'-tgatgcggccctcgagctactgaaacagaatctggtttataatgc tttc-3'

C2-IF-F:
                                            (SEQ ID NO: 31)
5'-ataaacaaacaaaccgcggaaaatgagtgccatatttccaagtgt tcccgag-3'

C2-IF-R:
                                            (SEQ ID NO: 32)
5'-tgatgcggccctcgagctactgaaacaaaatctggttaaatatac tctc-3'

D1-IF-F:
                                            (SEQ ID NO: 33)
5'-ataaacaaacaaaccgcggaaaatgagtcaggaaatattcaaaaa cattccc-3'

D1-IF-R:
                                            (SEQ ID NO: 34)
5'-tgatgcggccctcgagtcactgaaacagtacctggttcacaatac tttc-3'

F-IF-F:
                                            (SEQ ID NO: 35)
5'-ataaacaaacaaaccgcggaaaatgtccaccgaaatattcccagg aatcaagcaaattc-3'

Figure 3:
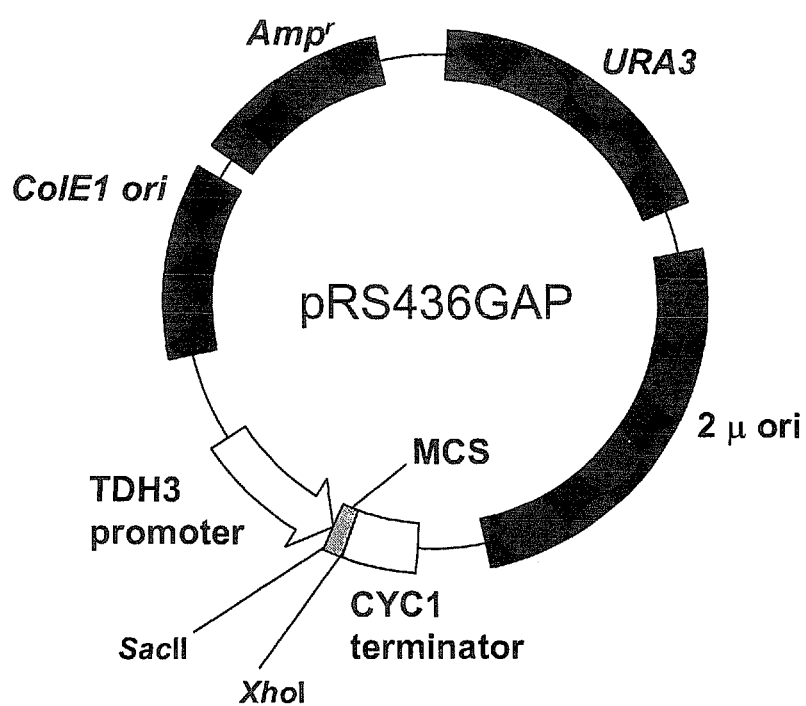
FIG. 3 shows a pRS436 GAP vector.

F-IF-R:
                                            (SEQ ID NO: 36)
5'-tgatgcggccctcgagttactgaaacagaatttgattaaacacac tttcgagatactcc-3'
``` v) Using the primer sets described in iv), PCR was performed with the amplified cDNA library described in i) as the template. The conditions for the PCR reaction were 30 cycles of [98° C. 10 sec, 55° C. 15 sec, 72° C. 2 min] using Prime-STAR HS DNA Polymerase (Takara Bio). The resulting four 1.4 kbp DNA fragments were named RsXI-C1, RsXI-C2, RsXI-D1 and RsXI-F, and were inserted into a pRS436GAP vector (DDBJ accession No. AB304862) (FIG. 3) digested with the restriction enzymes SacII and XhoI using In-Fusion Advantage™ PCR Cloning Kit (Takara Bio). The sequences of the DNA fragments inserted into pRS436GAP were analyzed using the primers TDH3-180F and CYC1t-100R. The sequences of the primers are shown below.

TDH3-180F: 5'-ccagttccctgaaattattccc-3' (SEQ ID NO: 37)

CYC1t-100R: 5'-cctagacttcaggttgtctaac-3' (SEQ ID NO: 38)

The nucleotide sequences of the four genes RsXI-C1, RsXI-C2, RsXI-D1 and RsXI-F discovered as a result of analysis are shown by SEQ ID NOS: 1, 3, 5 and 7, while the corresponding amino acid sequences are shown by SEQ ID NOS: 2, 4, 6 and 8. Apart from these sequences, four other genes RsXI-A, RsXI-B, RsXI-D2 and RsXI-E were also obtained by methods similar to those described above.

Table 1 shows the identity between the amino acid sequences converted from these 8 gene sequences and an amino acid sequence converted from a xylose isomerase gene (Genebank accession No. AJ249909) from *Piromyces* sp. E2. Amino acid sequence identity was determined using the protein blast (scoring parameters set to default) of BLAST (Basic Local Alignment Search Tool (blast.ncbi.nlm.nih.gov/Blast.cgi)) as the analysis program.

TABLE 1

| Name | Identity of amino acid sequence (%) |
|---|---|
| RsXI-A | 66 |
| RsXI-B | 66 |
| RsXI-C1 | 51 |
| RsXI-C2 | 50 |
| RsXI-D1 | 52 |
| RsXI-D2 | 50 |
| RsXI-E | 51 |
| RsXI-F | 52 |
| MdXI12 | 75 |
| MdXI19 | 74 |
| MdXI93 | 72 |

Figure 4:
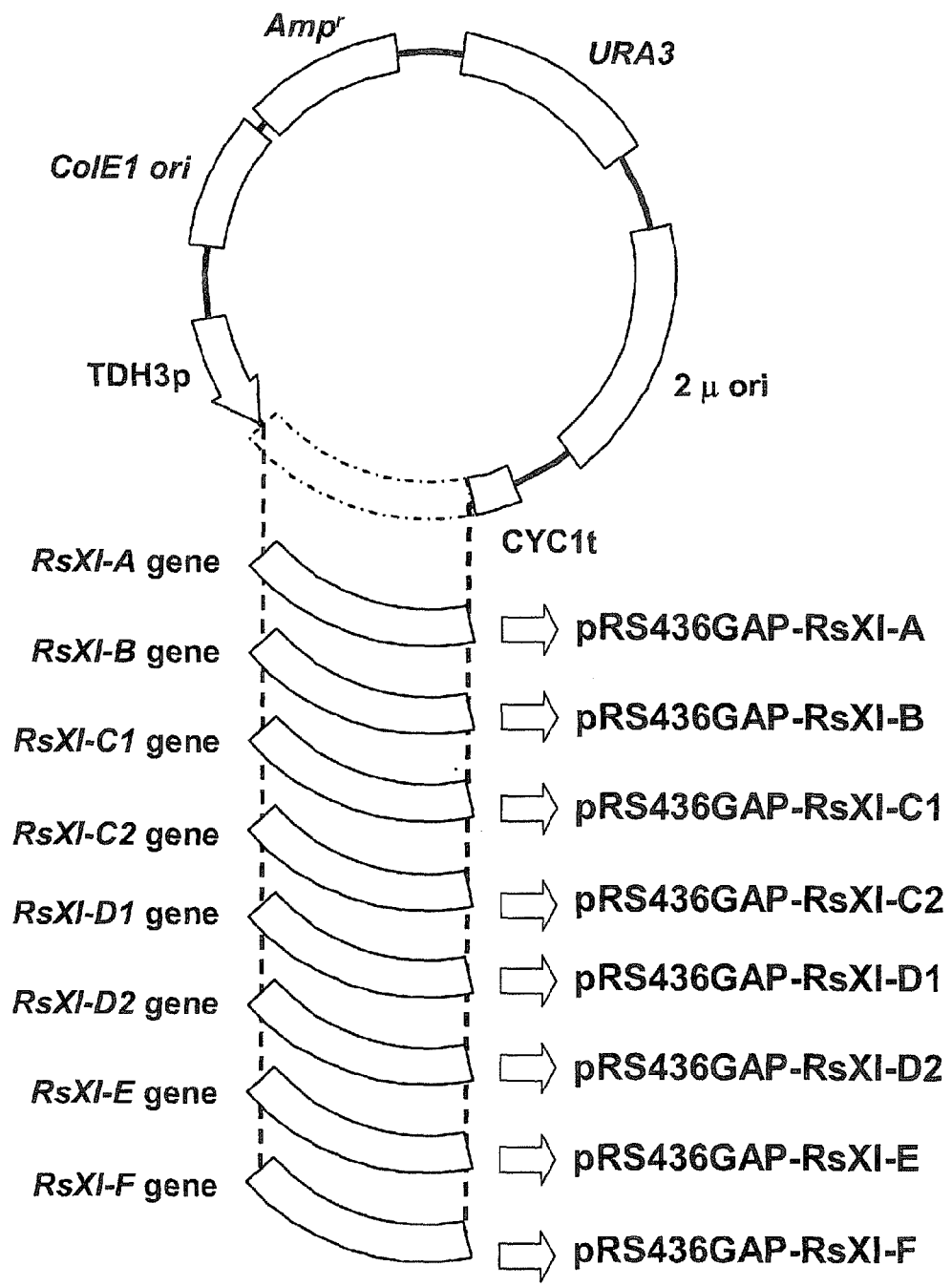
FIG. 4 shows yeast expression vectors for the obtained genes.

The yeast expression vectors prepared using each gene fragment were named pRS436GAP-RsXI-A, -B, -C1, -C2, -D1, -D2, -E and -F, respectively (FIG. 4). These vectors include gene sequences comprising a TDH3 promoter from *Saccharomyces cerevisiae* added to the 5' end and a CYC1 terminator from *S. cerevisiae* added to the 3' end of the inserted gene, as well as the gene sequence of a yeast autonomous replication factor 2μ ori, and the gene sequence of URA3 as an auxotrophic marker.

Example 2

Obtaining Genes from *Mastotermes darwiniensis* Intestinal Protist

Figure 5:
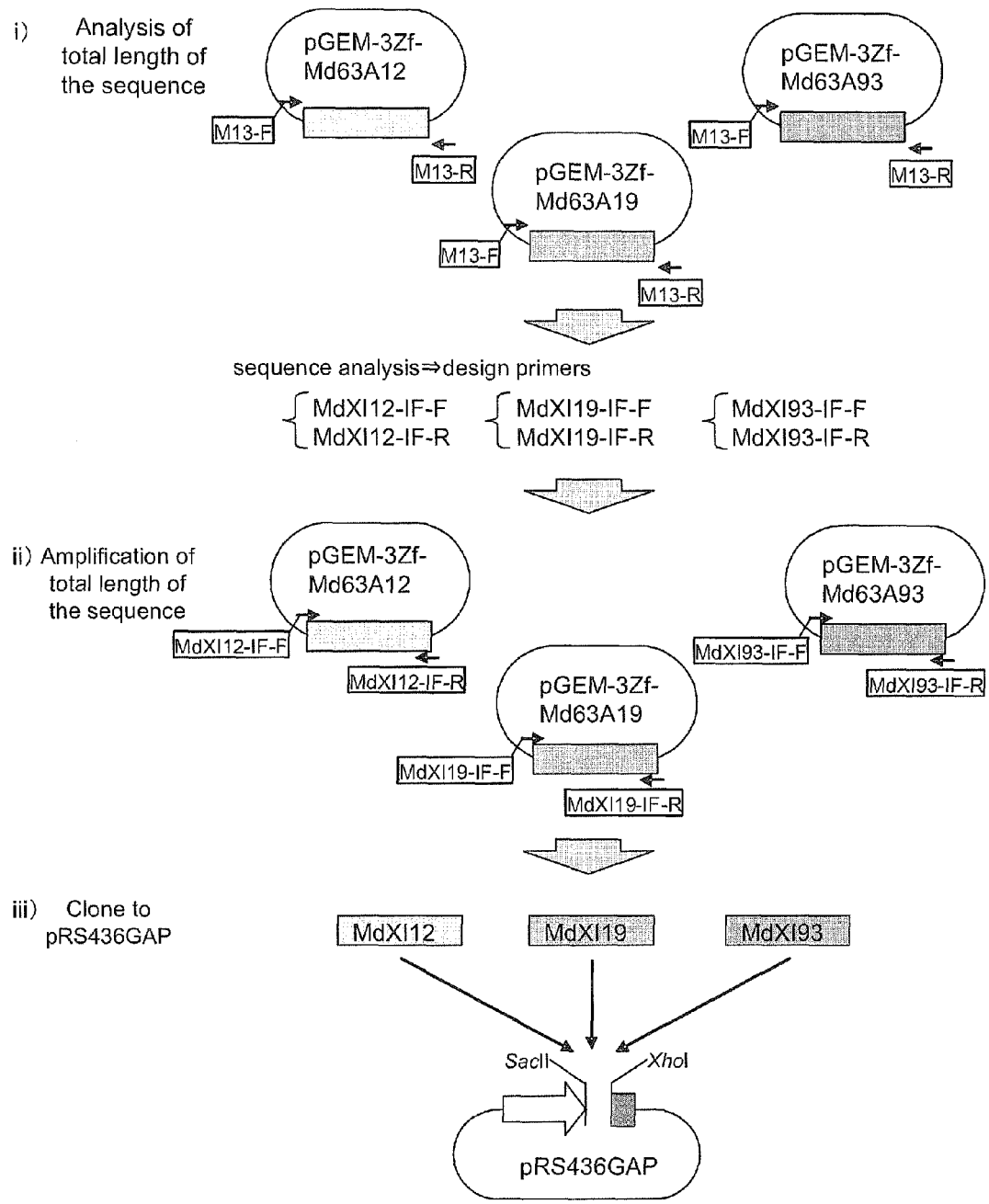
FIG. 5 shows procedures for obtaining xylose isomerase genes from a *Mastotermes darwiniensis* cDNA library.

Xylose isomerase-like genes were obtained from a *Mastotermes darwiniensis* intestinal protist. The test procedures are shown in FIG. 5 below. The procedures i) through iii) in FIG. 5 are explained in sequence below.

i) Three different genes corresponding to xylose isomerases were confirmed as a result of a homology analysis using partial sequences from the *Mastotermes darwiniensis* intestinal protist cDNA library described in Japanese Patent Application No. 2007-053122. However, only the partial sequences of the genes were known, and it was necessary to analyze their full-length sequences. A sequence analysis was therefore performed with the primers M13-F (SEQ ID NO: 19) and M13-R (SEQ ID NO: 20) using the plasmids pGEM-3Zf-Md06BA12, pGEM-3Zf-Md63A19 and pGEM-3Zf-Md63A93 carrying the full lengths of the corresponding genes as the templates.

The nucleotide sequences of the three genes MdXI12, MdXI19 and MdXI93 discovered as a result of analysis are shown by SEQ ID NOS: 9, 11 and 13, and the corresponding amino acid sequences are shown by SEQ ID NOS: 10, 12 and 14, respectively. Table 1 shows the identity between the amino acid sequences converted from these gene sequences and the amino acid sequences converted from a xylose isomerase gene sequence from *Piromyces* sp. E2. Amino acid sequence identity was determined using the protein blast (scoring parameters set to default) of BLAST (Basic Local Alignment Search Tool (blast.ncbi.nlm.nih.gov/Blast.cgi) as the analysis program.

Primers for amplifying the full sequences of each gene were prepared based on the discovered sequence information. The sequences of the prepared primers are shown below.

MdXI12-IF-F:
(SEQ ID NO: 39)
5'-ataaacaaacaaaccgcggaaaatgtctcacgaatactttccagg-3'

MdXI12-IF-R:
(SEQ ID NO: 40)
5'-tgatgcggccctcgagttattggaacatcgtcactatc-3'

MdXI19-IF-F:
(SEQ ID NO: 41)
5'-ataaacaaacaaaccgcggaaaatgtctggcgaatactttccagg-3'

MdXI19-IF-R:
(SEQ ID NO: 42)
5'-tgatgcggccctcgagtcattggaacgtcgtcactatg-3'

MdXI93-IF-F:
(SEQ ID NO: 43)
5'-ataaacaaacaaaccgcggaaaatgtctcgcgaatactttccagg-3'

Figure 6:
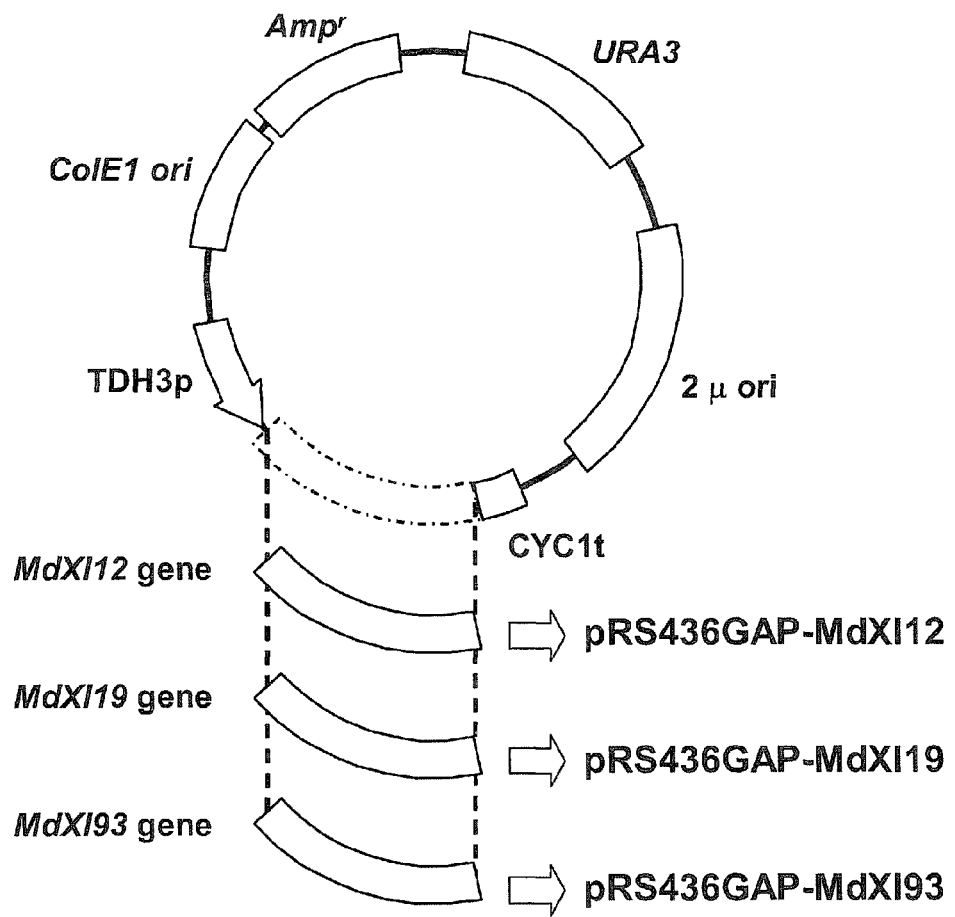
FIG. 6 shows yeast expression vectors for the obtained genes.

MdXI93-IF-R:
(SEQ ID NO: 44)
5'-tgatgcggccctcgagtcactggtacattgttacgattag-3' ii) The full length of each gene was amplified by PCR with the primer sets described in i), using MDXI12-IF-F with MdXI12-IF-R, MdXI19-IF-F with MdXI19-IF-R and MdXI93-IF-F with MdXI93-IF-R, and with pGEM-3Zf-Md06BA12, pGEM-3Zf-Md63A19 and pGEM-3Zf-Md63A93 as the templates, respectively. The conditions for the PCR reaction were 30 cycles×[98° C. 10 sec, 55° C. 15 sec, 72° C. 2 min] using PrimeSTAR HS DNA Polymerase (Takara Bio).

iii) Using an In-Fusion Advantage™ PCR Cloning Kit (Takara Bio), the three resulting 1.4 kbp DNA fragments were inserted into pRS436GAP (DDBJ Accession No. AB304862) (FIG. 2) digested with the restriction enzymes SacII and XhoI. Next, correct insertion of the genes into pRS436GAP was confirmed using the primers TDH3-180F (SEQ ID NO: 37) and CYC1t-100R (SEQ ID NO: 38). The prepared yeast expression vectors were named pRS436GAP-MdXI12, -MdXI19 and -MdXI93, respectively (FIG. 6). These vectors include gene sequences comprising the TDH3 promoter added to the 5' end and the CYC1 terminator added to the 3' end of the inserted gene, as well as the gene sequence of a yeast autonomous replication factor 2μ ori, and the gene sequence of URA3 as an auxotrophic marker.

Example 3

Preparation of Transformed Yeast (Preparation of Yeast Expression Vectors for Known Xylose Isomerase Genes)

Figure 7:
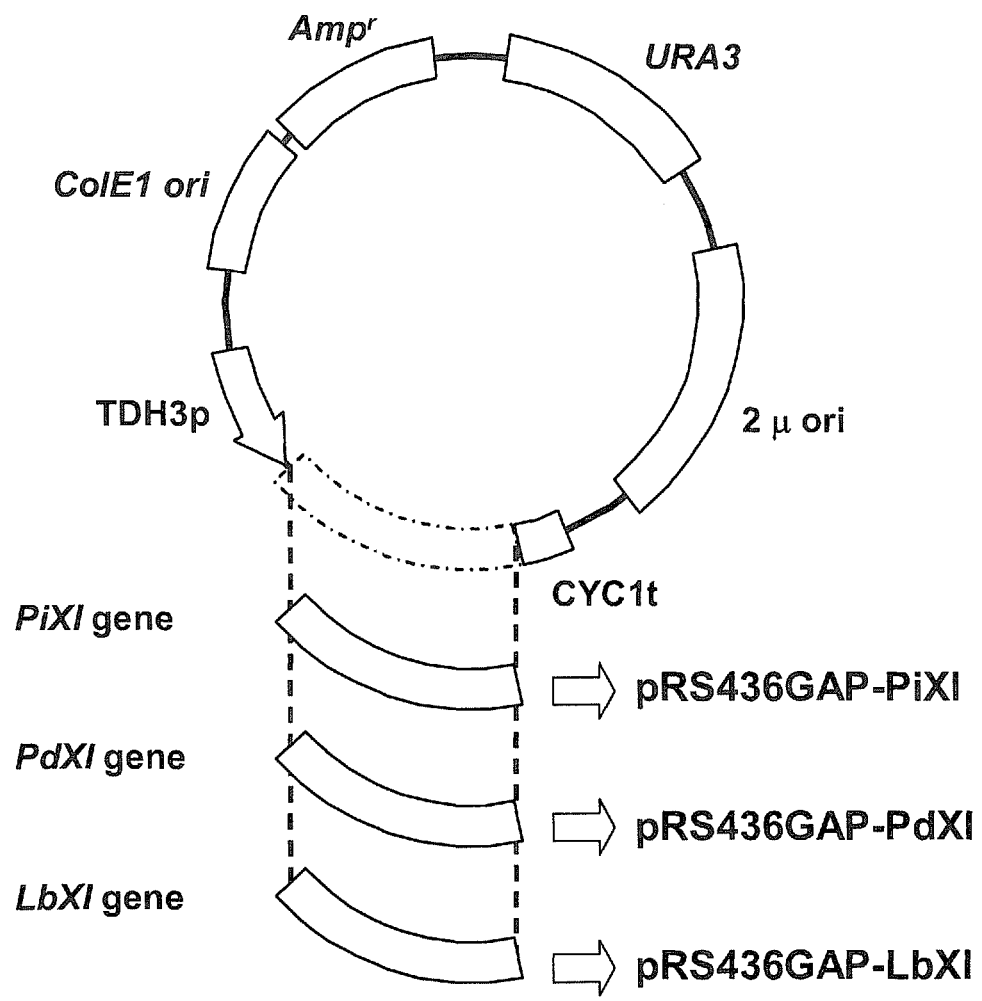
FIG. 7 shows yeast expression vectors for known XI genes.

Yeast expression vectors pRS436GAP-PiXI, -PdXI and -LbXI (FIG. 7) were prepared for a xylose isomerase gene (PiXI) from *Piromyces* sp. E2, a xylose isomerase (protein ID: YP_001302175) gene (PdXI) from *Parabacteroides distasonis* ATCC 8503 having 73% amino acid sequence identity with PiXI, and a xylose isomerase (protein ID: EAQ50619) gene (LbXI) from *Leeuwenhoekiella blandensis* MED217 having 64% sequence identity. These vectors included gene sequences comprising the TDH3 promoter added to the 5' end and the CYC1 terminator added to the 3' end of the inserted gene including PiXI gene, as well as the gene sequence of a yeast autonomous replication factor 2μ ori, and the gene sequence of URA3 as an auxotrophic marker.

(Preparation of Pentose Phosphate Pathway Enhanced Yeast)

Using the vectors pXhisHph-HOR7p-ScXK, pXAd3H-HOR7p-ScTAL1-ScTKL1 and pXGr3L-HOR7p-ScRPE1-ScRKI1 explained below, yeast strains was prepared overexpressing the XKS1, TAL1, TKLJ, RPE1 and RKI1 genes, while having the GRE3 gene deleted. These vectors are shown together in FIG. 8. The media used in the following examples are shown all together in Table 2.

(1) XK Gene Expression Vector

Figure 8:
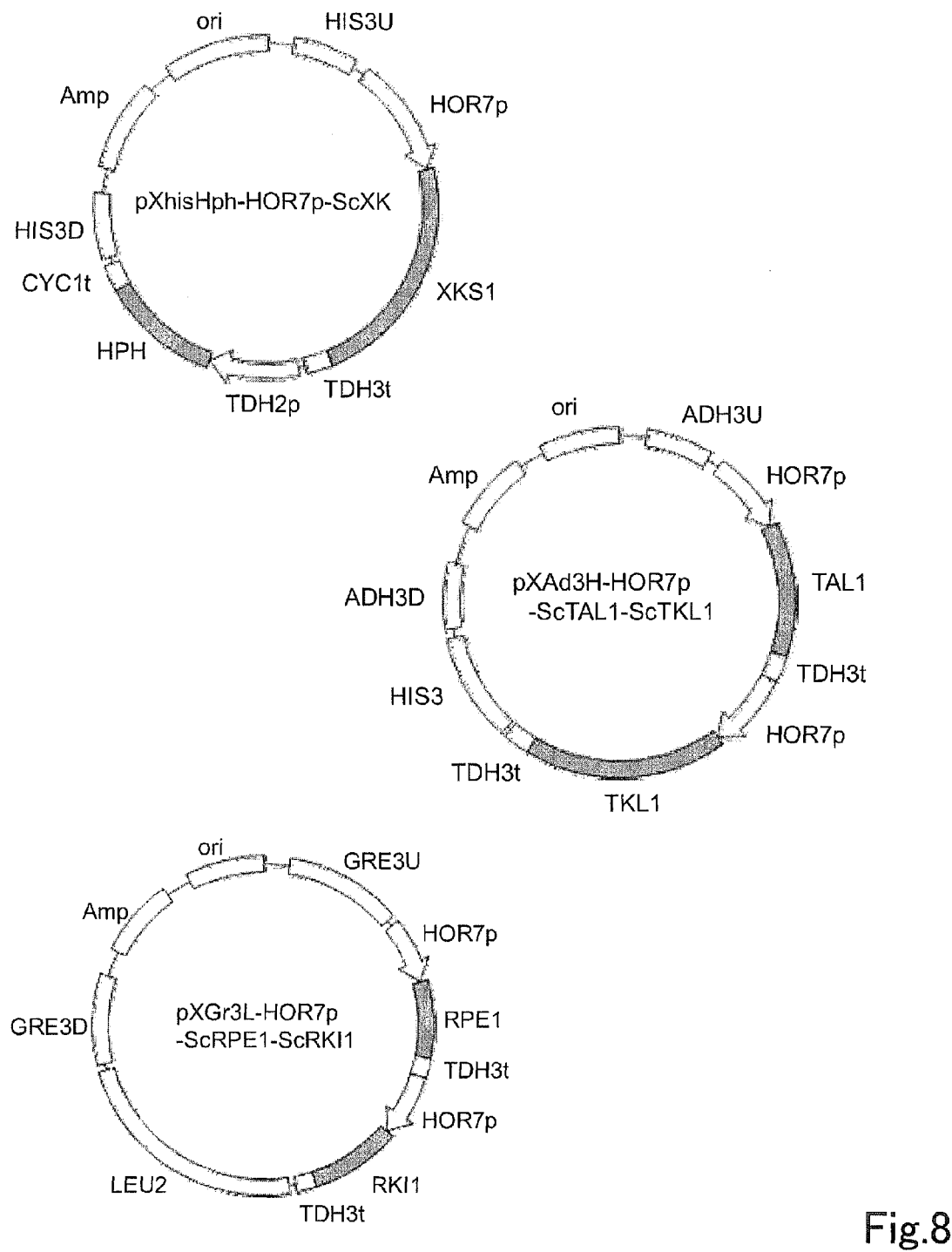
FIG. 8 shows yeast expression vectors of pentose phosphate pathway enzyme genes.

A yeast expression vector pXhisHph-HOR7p-ScXK was prepared for a xylulokinase (XK) gene from the yeast *S. cerevisiae* (FIG. 8). This vector was constructed so as to include a gene sequence comprising the XK gene XKSJ (genebank No. X61377) from *S. cerevisiae* NBRC304 with the HOR7 promoter added to the 5' end and the TDH3 terminator added to the 3' end, as well as the gene sequence (HIS3U) of a roughly 500 bp region upstream and the gene sequence (HIS3D) of a roughly 500 bp region downstream from the histidine synthase (HIS3) gene as regions of homologous recombination with the yeast genome, and a gene sequence comprising a hygromycin phosphotransferase (hph) gene with the TDH2 promoter added to the 5' end and the CYC1 terminator added to the 3' end as a marker.

(2) TAL1, TKL1 Gene Expression Vectors

A yeast expression vector pXAd3H-HOR7p-ScTAL1-ScTKL1 (FIG. 8) was prepared for the *S. cerevisiae* transaldolase 1 gene (TAL1) and transketolase 1 gene (TKL1). This vector was constructed so as to include a gene sequence comprising a gene TAL1 gene (Genbank: U19102) from *S. cerevisiae* S288C with the HOR7 promoter added to the 5' end and the TDH3 terminator added to the 3' end, a gene sequence comprising a TKL1 gene (Genbank: X73224) from *S. cerevisiae* S288 with the HOR7 promoter added to the 5' end and the TDH3 terminator added to the 3' end, the gene sequence (ADH3U) of a roughly 500 bp region upstream and the gene sequence (ADH3D) of a roughly 500 bp region downstream from the alcohol dehydrogenase 3 (ADH3) gene as a region of homologous recombination with the yeast genome, and a gene sequence (HIS3 marker) comprising a histidine synthase (HIS3) gene as a marker.

(3) RPE1, RKI1 Gene Introduction Vectors

A yeast introduction vector pXGr3L-HOR7p-ScRPE1-ScRKI1 (FIG. 8) was prepared for a ribulose phosphate epimerase 1 gene (RPE1) and a ribose phosphate ketoisomerase gene (RKI1) from *S. cerevisiae*. This vector was constructed so as to include a gene sequence comprising a RPE1 gene (Genbank: X83571) from *S. cerevisiae* S288 with the HOR7 promoter added to the 5' end and the TDH3 terminator added to the 3' end, a gene sequence comprising a RKI1 gene (Genbank: Z75003) from *S. cerevisiae* S288 with the HOR7 promoter added to the 5' end and the TDH3 terminator added to the 3' end, a roughly 1000 bp gene sequence (GRE3U) upstream from the GRE3 gene and the gene sequence (GRE3D) of a roughly 800 bp region comprising about 500 bp of the 3' region of the GRE3 gene as regions for homologous recombination with the yeast genome and for destroying the aldose reductase 3 (GRE3) gene, and a gene sequence (LEU2 marker) comprising a leucine synthase (LEU2) gene as a marker.

TABLE 2

| Medium name | Composition of the medium |
| --- | --- |
| SD medium | 6.7 g/L Yeast Nitrogen Base without amino acids, 20 g/LD-Glucose |
| SX medium | 6.7 g/L Yeast Nitrogen Base without amino acids, 20 g/L D-Xylose |
| SD-HLU Liquid medium | |
| Add 50 x amino acid mixture solution (-HLU) to SD medium at a fiftieth volume of the SD medium | |
| SX-HLU Liquid medium | |
| Add 50 x amino acid mixture solution (-HLU) to SX medium at a fiftieth volume of the SX medium | |
| SD Agar medium | |
| SD medium + 20 g/L Agar | |
| SD-H Agar medium | |
| Add 50 x amino acid mixture solution (-H) to SD Agar medium at a fiftieth volume of the SD Agar medium | |
| SD-HL Agar medium | |
| Add 50 x amino acid mixture solution (-HL) to SD Agar medium at a fiftieth volume of the SD Agar medium | |
| SD-HLU Agar medium | |
| Add 50 x amino acid mixture solution (-HLU) to SD Agar medium at a fiftieth volume of the SD Agar medium | |
| 50 x amino acid mixture solution (-H) | 1 g/L L-adenine sulfate, 5 g/L L-Leucine, 1 g/L L-tryptophan, 1 g/L Uracil |
| 50 x amino acid mixture solution (-HL) | 1 g/L L-adenine sulfate, 1 g/L L-tryptophan, 1 g/L Uracil |
| 50 x amino acid mixture solution (-HLU) | 1 g/L L-adenine sulfate, 1 g/L L-tryptophan |
| YPD + HYG medium | 10 g/L Yeast Extract, 20 g/L Polypeptone, 20 g/L Glucose, 150 mg/L Hygromycin |

Yeast transformation was performed using Frozen-EZ Yeast Transformation II (Zymo Research) in accordance with the attached protocols. First, the yeast strain *S. cerevisiae* MT8-1 as the host was transformed with the pXhis-Hph-HOR7p-ScXK vector using a fragment digested with the restriction enzyme Sse83871, then spread on YPD+HYG agar medium, and the colonies were purified by streak culturing growing viable on new YPD+HYG agar medium. The purified selected strain was named PP100. Next, the PP100 strain was transformed using a fragment of the pXAd3H-HOR7p-ScTAL1-ScTKL1 vector digested with the restriction enzyme Sse83871, and then spread on SD-H agar medium, and the colonies were purified by streak culturing viable colonies on new SD-H agar medium. The purified selected strain was named PP300. Next, the PP300 strain was transformed using a fragment of the pXGr3L-HOR7p-ScRPE1-ScRKI1 vector digested with the restriction enzyme Sse83871, and then spread on SD-HL agar medium, the colonies were purified by streak culturing viable colonies on new SD-HL agar medium. The purified selected strain was named PP600.

(Gene Introduction into Yeast)

The PP600 strain was transformed using the prepared yeast introduction vectors for each gene, and then spread on SD-HLU agar medium (Table 2), and the colonies were purified by streak culturing viable colonies on new SD-HLU agar medium. The names of the purified selected strains and the introduced genes and vectors used are shown in Table 3.

TABLE 3

| Strain | Gene | Vector |
|---|---|---|
| PP600/pRS436GAP-RsXI-A | RsXI-A | pRS436GAP-RsXI-A |
| PP600/pRS436GAP-RsXI-B | RsXI-B | pRS436GAP-RsXI-B |
| PP600/pRS436GAP-RsXI-C1 | RsXI-C1 | pRS436GAP-RsXI-C1 |
| PP600/pRS436GAP-RsXI-C2 | RsXI-C2 | pRS436GAP-RsXI-C2 |
| PP600/pRS436GAP-RsXI-D1 | RsXI-D1 | pRS436GAP-RsXI-D1 |
| PP600/pRS436GAP-RsXI-D2 | RsXI-D2 | pRS436GAP-RsXI-D2 |
| PP600/pRS436GAP-RsXI-E | RsXI-E | pRS436GAP-RsXI-E |
| PP600/pRS436GAP-RsXI-F | RsXI-F | pRS436GAP-RsXI-F |
| PP600/pRS436GAP-MdXI12 | MdXI12 | pRS436GAP-MdXI12 |
| PP600/pRS436GAP-MdXI19 | MdXI19 | pRS436GAP-MdXI19 |
| PP600/pRS436GAP-MdXI93 | MdXI93 | pRS436GAP-MdXI93 |
| PP600/pRS436GAP-PdXI | PdXI | pRS436GAP-PdXI |
| PP600/pRS436GAP-LbXI | LbXI | pRS436GAP-LbXI |
| IX700m | PiXI | pRS436GAP-PiXI |
| IX700mc | — | pRS436GAP |

(XI Activity Measurement in Transformed Yeasts)

The prepared strains with the various introduced genes were cultured for 24 hours in SD-HLU liquid medium (Table 2), and the cells were collected and washed twice with sterile water, and then washed twice with 100 mM phosphate buffer (pH 7.0). Glass beads (acid washed di. 425 to 600 μm: Sigma) and 100 mM phosphate buffer (pH 7.0) were added to the yeast pellets after washing, and these were agitated for 15 minutes at 4° C. in a Micromixer E-36 (TAITEC) to disrupt the yeast cells. These were then centrifuged for 5 minutes at 12000 rpm at 4° C., and the supernatant was collected as a crude yeast extract. The total protein concentration of the crude yeast extract was measured with a Quick Start protein assay kit (Bio-Rad).

Figure 9:
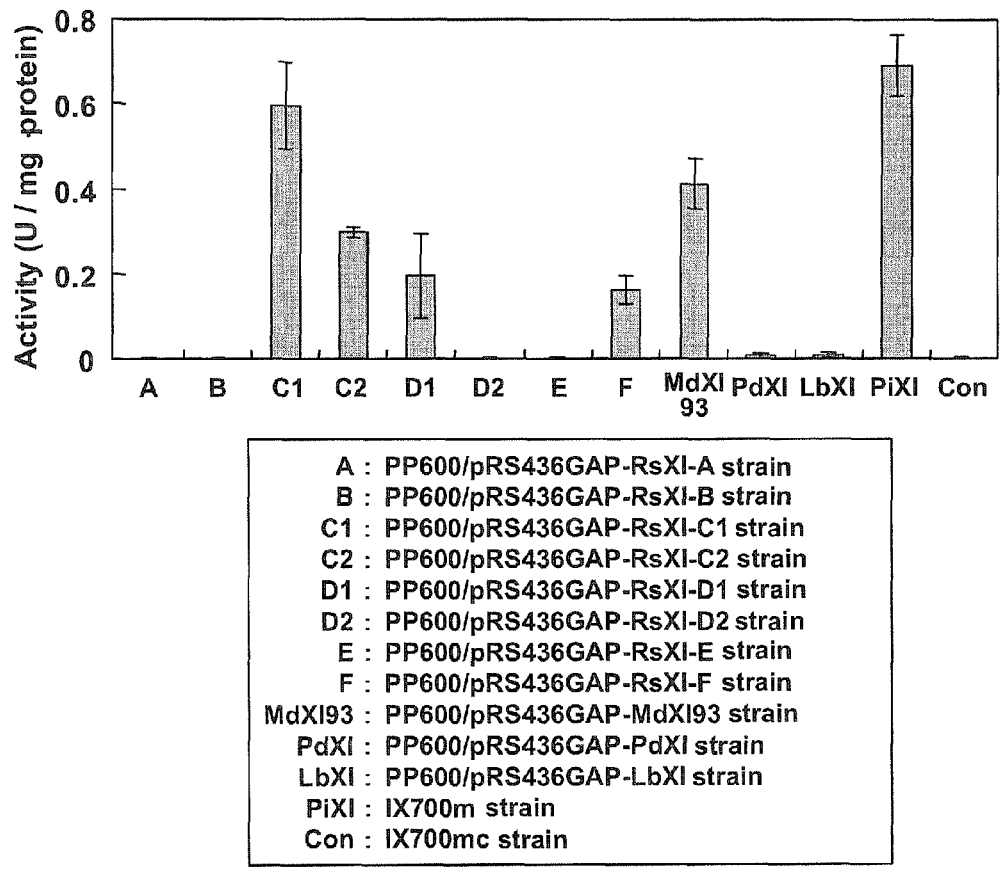
FIG. 9 shows XI activity measurement results for yeast extracts.

Next, the XI activity of the crude yeast extract was measured with reference to the XI activity measurement methods described in Japanese Patent Application Publication No. 2008-079564. Specifically, the crude yeast extract was added to a reaction liquid containing 50 mM maleic acid buffer (pH 6.85), 10 mM $MgSO_4$, 1 mM $CoCl_2$, 1 mM $MnCl_2$ and 10 mM xylose, and reacted for 30 minutes at 30° C., after which the xylose was assayed by the cysteine-carbazole method (Zacharias Dische and Ellen Borefreund, J. Biol. Chem. 192: 583-587 (1951)), and XI activity was measured. In the cysteine-carbazole method, cysteine-carbazole-sulfate solution was added after the aforementioned reaction, a color reaction was performed at 30° C. for 30 minutes, and absorbancy was measured at a wavelength of 540 nm. FIG. 9 shows the results of XI activity measurement. Activity was defined as 1 U of activity producing 1 μmol of xylulose in 1 minute, divided by the protein concentration of the raw yeast extract (U/mg-protein).

As shown in FIG. 9, no XI activity was seen with the IX700mc strain having no introduced XI gene or with the strains having the known XI genes, PdXI and LbX, introduced therein, and no XI activity was seen with the strains having RsXI-A, -B, -D2 and -E introduced therein. However, XI activity was confirmed with the IX700m strain having the introduced PiXI gene, and XI activity was also confirmed with the strains having the introduced RsXI-C1, -C2, -D1, -F and MdXI93 genes. Of these, the XI activity of the PP600/pRS436GAP-RsXI-C1 strain having the introduced RsXI-C1 gene was equivalent to the activity of the IX700m strain having the introduced PiXI gene. This confirms that the proteins produced in yeast cells based on the RsXI-C1, -C2, -D1, -F and MdXI93 genes have XI activity.

(Growth Test of Transformed Yeasts Using Xylose as the Carbon Source)

Figure 10:
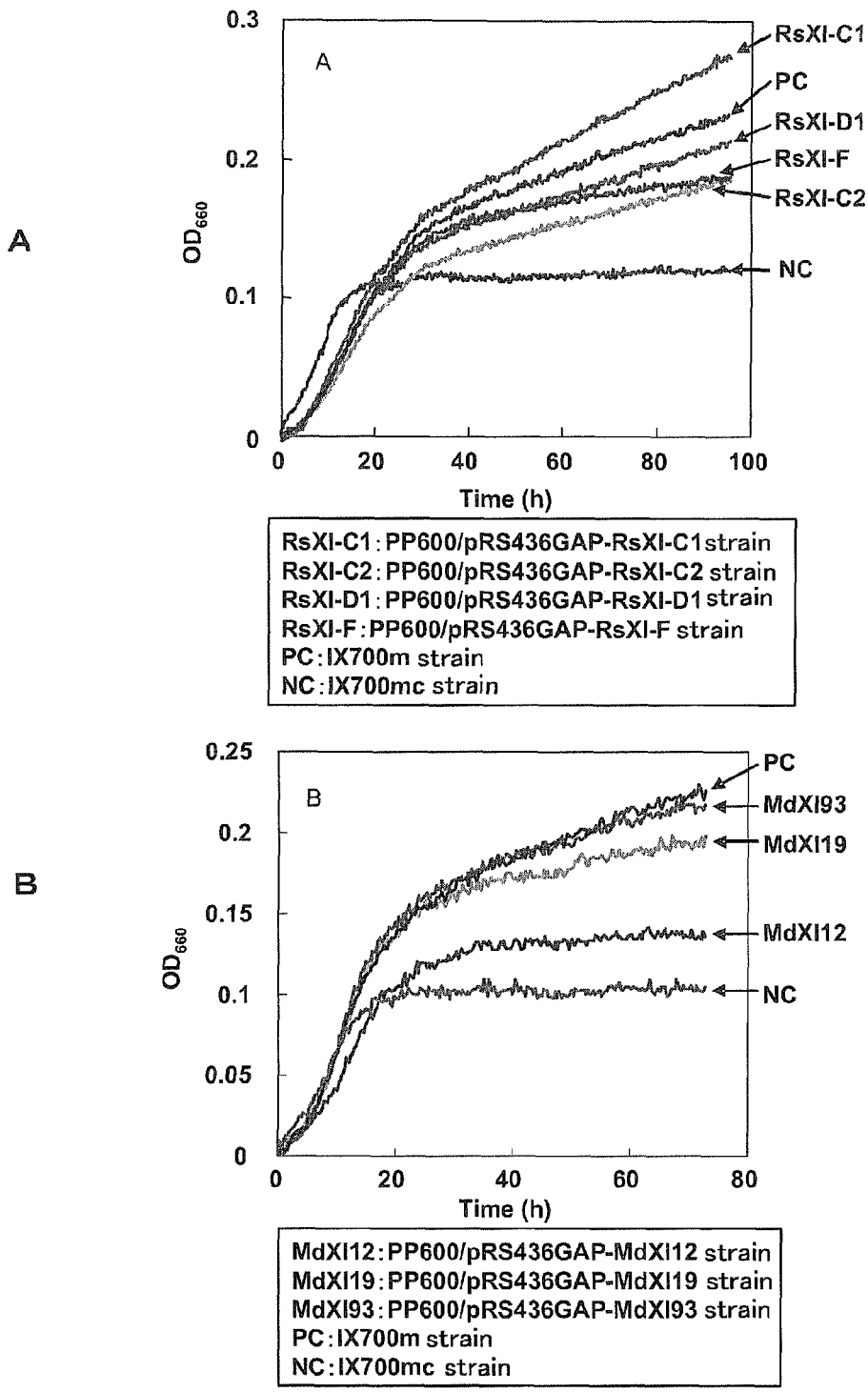
FIG. 10 shows growth test results using xylose as a carbon source.

To evaluate the xylose utilization ability of each of the transformed yeasts, a growth test was performed in medium having xylose as a sole carbon source. The IX700m strain, IX700mc strain, PP600/pRS436GAP-RsXI-C1 strain, PP600/pRS436GAP-RsXI-C2 strain, PP600/pRS436GAP-RsXI-D1 strain, PP 600/pRS436GAP-RsXI-F strain, PP600/pRS436GAP-MdXI12 strain, PP600/pRS436GAP-MdXI19 strain and PP600/pRS436GAP-MdXI93 strain were cultured for 24 hours in SD-HLU liquid medium, and the cells were collected and washed twice with sterile water and then added to SX-HLU liquid medium (Table 1) prepared in an L-shaped test tube to initiate the growth test. For the growth test, the OD (660 nm) of the culture liquid was measured at 20 minute intervals under culture conditions of 30° C., 70 rpm using a TVS062CA Biophotorecorder (Advantec). The results of the growth test are shown in FIG. 10.

In FIG. 10A, no increase in medium OD was seen after 20 hours with the IX700mc strain having no introduced XI gene, but increases in medium OD were seen after 20 hours with the PP600/pRS436GAP-RsXI-C1 strain, PP600/pRS436GAP-RsXI-C2 strain, PP600/pRS436GAP-RsXI-D1 strain and PP600/pRS436GAP-RsXI-F strain and the IX700m strain having the introduced PiXI gene, confirming yeast cell growth on xylose. This shows that growth on xylose as a carbon source is possible by introducing the RsXI-C1, RsXI-C2, RsXI-D1 and RsXI-F genes into yeast. The growth rate after 40 hours was 0.096 $OD_{660}h^{-1}$ with the IX700m strain but 0.126 $OD_{660}h^{-1}$ with the PP600/pRS436GAP-RsXI-C1 strain, confirming that the proliferation rate of the PP600/pRS436GAP-RsXI-C1 strain was 1.3 higher than that of the IX700m strain.

Similarly, in FIG. 10B, no increase in medium OD was seen after 20 hours with the IX700mc strain having no introduced XI gene, but increases in medium OD were seen after 20 hours with PP600/pRS436GAP-MdXI12, -MdXI19 and -MdXI93 and with the IX700m strain having the introduced PiXI gene, confirming yeast cell growth. This shows that growth on xylose as a carbon source is possible by introducing the MdXI12, MdXI19 and MdXI93 genes into yeast. At the same time, this also shows that the proteins coded by these genes have XI activity in yeasts and other eukaryotic cells.

The seven genes confirmed by these results to have xylose isomerase activity in yeast were converted to amino acid sequences, and the sequence identities were compared, with the results shown in Table 4. Amino acid sequence identity was determined using the homology search function (program: fastp (Protein-Protein), parameters set to default) of Genetix gene analysis software (Genetyx).

TABLE 4

|  | 1 | 2 | 3 | 4 | 5 | 6 | 7 |
|---|---|---|---|---|---|---|---|
| 1 RsXI-C1 |  |  |  |  |  |  |  |
| 2 RsXI-C2 | 87 |  |  |  |  |  |  |
| 3 RsXI-D1 | 91 | 86 |  |  |  |  |  |
| 4 RsXI-F | 85 | 82 | 84 |  |  |  |  |
| 5 MdXI12 | 49 | 50 | 51 | 51 |  |  |  |
| 6 MdXI19 | 50 | 52 | 52 | 52 | 94 |  |  |
| 7 MdXI93 | 49 | 51 | 51 | 51 | 85 | 86 |  |

As shown in Table 4, the results of the identity comparison show a high degree of identity (82% or more) among RsXI-C1, RsXI-C2, RsXI-D1 and RsXI-F, and a high degree of identity (85% or more) among MdXI12, MdXI19 and MdXI93. However, the degree of identity between the RsXI group and MdXI group was low (52% or less), and given that these groups derive from different protist cDNA libraries, this suggests that they are different lines of XI.

Example 4

(1) Synthesis of Xylose Isomerase Genes Suited to Yeast Expression, and Preparation of Yeast Expression Vectors Synthetic genes were prepared comprising optimized codons for yeast expression matched with RsXI-C1, PiXI and the gene (CpXI) of a *Clostridium phytofermentans* xylose isomerase (protein ID: YP_001558336) that has been reported to be active in yeasts (Non-patent Literature 1). The genes were synthesized by Genscript Corporation (www.Genscript.com) and Life Technologies Corporation (www.lifetechnologies.com), and the synthesized genes were named RsXIC1-O (SEQ ID NO: 45), PiXI-O (SEQ ID NO: 46) and CpXI-O (SEQ ID NO: 47), respectively.

Next, RsXIC1-O, PiXI-O and CpXI-O were amplified by PCR. The sequences of the primers used are shown below.

```
RsXIC1-O-IF-F:
                                      (SEQ ID NO: 48)
5'-ataaacaaacaaaccgcggaaaatgtctcaaattttaaggata
tccc-3'

RsXIC1-O-IF-R:
                                      (SEQ ID NO: 49)
5'-tgatgcggccctcgagttattgaaacaaaatttggttaataatac
tttc-3'

PiXI-O-IF-F:
                                      (SEQ ID NO: 50)
5'-ataaacaaacaaaccgcggaaaatggctaaggaatacttcc-3'

PiXI-O-IF-R:
                                      (SEQ ID NO: 51)
5'-tgatgcggccctcgagttattggtacatagcaacaattgcttc-3'

CpXI-O-IF-F:
                                      (SEQ ID NO: 52)
5'-ataaacaaacaaaccgcggaaaatgaagaattacttcccaaatg
tccc-3'

CpXI-O-IF-R:
                                      (SEQ ID NO: 53)
5'-tgatgcggccctcgagtcatctaaacaagatgttattgacaatagt
ctc-3'
```

The PCR amplified gene fragments were introduced into pRS436GAP digested with the restriction enzymes SacII and XhoI, and the prepared yeast gene expression vectors were named pRS436GAP-RsXIC1-O, pRS436GAP-PiXI-O and pRS436GAP-CpXI-O, respectively.

(2) Introduction of Codon Optimized Xylose Isomerase Genes in Yeast

Yeast strains capable of utilizing xylose were prepared using optimized XI gene yeast expression vectors. The yeasts were transformed using Frozen-EZ Yeast Transformation II (Zymo Research) in accordance with the attached protocols.

First, the TRP1 gene (Gene ID: 851570) and its neighboring region were amplified by PCR using genome DNA from *S. cerevisiae* S288 as the template. The resulting amplification product was used to transform the W600 strain described in Japanese Patent Application No. 2010-063703, which overexpresses the XKS1, TAL1, TKL1, RPE1 and RKI1 genes while having the GRE3 gene broken. This was then spread on SD+U agar medium (SD agar medium containing 20 mg/L uracil), and pure colonies were obtained by streak culturing viable colonies on new SD+U medium. The purified selected strain was named W600W. The primers shown below were used in PCR amplification of the TRP1 gene and neighboring region.

TRP1M-F: 5'-aacgacattactatatatataatatagg-3' (SEQ ID NO: 54)
TRP1M-R: 5'-caagtgcacaaacaatac-3' (SEQ ID NO: 55)

Next, pRS436GAP-RsXIC1-O, pRS436GAP-PiXI-O and pRS436GAP-CpXI-O were each used to transform W600W, which was then spread on SD agar medium, and pure colonies were obtained by streak culturing viable colonies on new SD agar medium. The purified selected strains were named W600W/pRS436GAP-RsXIC1-O, W600W/pRS436GAP-PiXI-O and W600W/pRS436GAP-CpXI-O, respectively. As a control, pRS436GAP was introduced by the same methods into W600W, and the resulting transformant was named W600W/pRS436GAP.

(3) Growth Test of Transformed Yeasts Using Xylose as a Carbon Source

To evaluate the xylose utilization ability of each of the transformed yeasts, a growth test was performed in medium having xylose as a carbon source. The W600W/pRS436GAP-RsXIC1-O, W600W/pRS436GAP-PiXI-O, W600W/pRS436GAP-CpXI-O and W600W/pRS436GAP strains were cultured for 24 hours in SD liquid medium, and the cells were collected and washed twice with sterile water and then added to SX liquid medium prepared in an L-shaped test tube to initiate the growth test.

Figure 11:
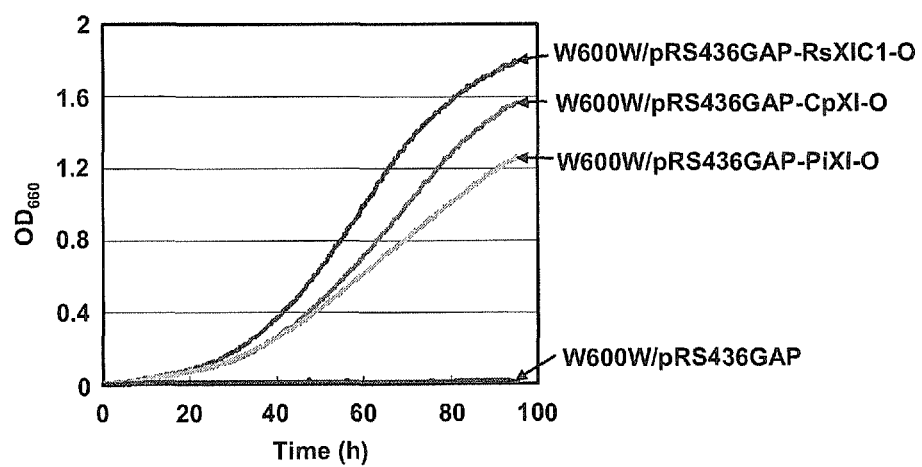
FIG. 11 shows growth test results using xylose as a carbon source with transformed yeasts having introduced xylose isomerase genes (RsXIC1-O, CpXI-O and PiXI-O) with optimized codons.

The results of the growth test are shown in FIG. 11. No increase in medium OD was seen with the W600W/pRS436GAP strain having no introduced XI, but increased medium OD was seen with the strains having the introduced XI genes, confirming cell growth on xylose. The specific growth rate during the period of medium $OD_{660}$ 0.1 to 0.5 was confirmed to be about 1.2 times higher for the W600W/pRS436GAP-RsXIC1-O strain than for the W600W/pRS436GAP-PiXI-O and W600W/pRS436GAP-CpXI-O strains (Table 5).

TABLE 5

| Strain | Specific growth rate($h^{-1}$) |
|---|---|
| W600W/pRS436GAP-RsXIC1-O | 0.071 ± 0.0004 |
| W600W/pRS436GAP-PiXI-O | 0.058 ± 0.0024 |
| W600W/pRS436GAP-CpXI-O | 0.060 ± 0.0017 |

(4) Comparison of Fermentation Ability in Glucose/Xylose Mixed Medium

Each transformed yeast strain was seeded in 50 ml of SD liquid medium, and cultured for 3 days to obtain seed culture. All of the seed culture was then added to 500 ml of SD liquid medium and cultured for 24 hours, and the cells were collected and washed twice with sterile water.

Figure 12:
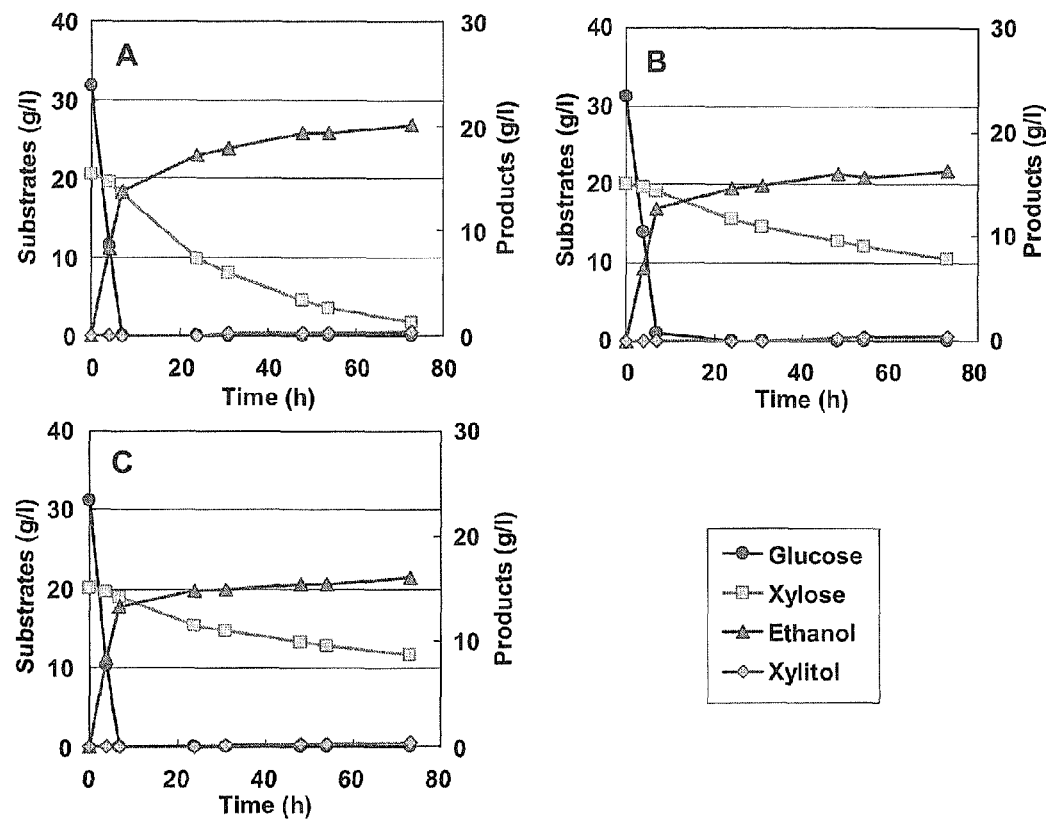
FIG. 12 shows fermentation test results using glucose and xylose as carbon sources with transformed yeasts having introduced xylose isomerase genes (RsXIC1-O, PiXI-O and CpXI-O) with optimized codons. The fermentation test results are respectively shown in (A) codon optimized RsXI-C1 introduction yeast, (B) codon optimized PiXI introduction yeast, and (C) codon optimized CpXI introduction yeast.

A 100 ml screw cap bottle having an exhaust line with a check valve attached to the lid was used for the fermentation test. 50 ml of SDX medium (6.7 g/l yeast nitrogen base without amino acids and nucleic acids, 30 g/l D-glucose, 20 g/l xylose) with liquid yeast suspension added to a final $OD_{600}$ of 10 of the fermentation medium was prepared, and fermentation was performed at 30° C., 100 rpm. The culture liquid was sampled periodically, and the substrate (glucose and xylose) and products (ethanol, glycerol and xylitol) were analyzed by liquid chromatography. An HPX-87H column (Bio-Rad) was used at 60° C. as the liquid chromatography column, and a RID-10A refractive index detector (Shimadzu Mfg.) was used as the detector. 0.05% sulfuric acid solution was used for the mobile phase, which was supplied at a rate of 0.6 ml/min. FIG. 12 shows changes over time in the substrate concentrations and product concentrations in fermentation medium of each transformant. The fermentation tests were performed twice or more, and the averages are given.

As shown in FIG. 12, mainly glucose was consumed at the initial stage of fermentation by all transformants, and xylose began to decline as the glucose was depleted. There was almost no accumulation of the by-product xylitol in any of the fermentations. In terms of xylose consumption, 10 g/l or more of xylose remained after 72 hours of fermentation with the W600W/pRS436GAP-PiXI-0 strain (FIG. 12(B)) and W600W/pRS436GAP-CpXI-O strain (FIG. 12(C)), but the xylose consumption rate of the W600W/pRS436GAP-RsXIC1-O strain (FIG. 12(A)) was about twice that of the other transformants, and almost all the xylose was consumed after 72 hours. These results show that in comparison with the known xylose isomerases PiXI-O and CpXI-O, RsXIC1-O is more effective at utilizing xylose in yeasts.

(5) Xylose Isomerase Kinetic Analysis

The W600W/pRS436GAP-RsXIC1-O strain and W600W/pRS436GAP-PiXI-O strain were cultured for 24 hours in SD liquid medium, and the cells were collected and washed twice with sterile water, and then washed twice with 100 mM phosphate buffer (pH 7.0). After washing, glass beads (di 0.3 mm, Yasui Kikai) and 100 mM phosphate buffer (pH 7.0) were added to the yeast pellets, and a Multi-beads shocker (Yasui Kikai) was operated for 7 minutes at 4° C., 2500 rpm to disrupt the yeast cells. The resulting disrupted cell liquid was centrifuged for 5 minutes at 4° C., 12000 rpm, and the supernatant was collected as a crude yeast extract. The total protein concentration of the crude yeast extract was measured with a Quick Start protein assay kit (Bio-Rad).

Next, xylose isomerase activity in the crude yeast extract was measured with reference to the xylose isomerase activity measurement methods described in Non-patent Literature 1. Specifically, xylose was added to reaction mixtures containing the crude yeast extract, 0.15 mM NADH, 10 mM $MgCl_2$, 2 U sorbitol dehydrogenase (SDH) and 100 mM Tris-HCl (pH 7.5) to initiate a reaction, and NADH oxidation attributable to conversion of xylulose to xylitol by SDH was measured. The reaction was performed at 30° C., and NADH absorbancy changes were measured at a wavelength of 340 nm with a Ubest-55 spectrometer (Jasco). For determination of kinetic parameters, reactions were performed with final xylose concentrations of 250 mM, 150 mM, 100 mM, 50 mM, 25 mM and 5 mM, and xylose isomerase activity was measured at each concentration. Table 6 shows the kinetic parameter of xylose isomerase in each crude yeast extract. The kinetic parameter was calculated by Hanes-Woolf plot (Non-patent Literature 6) based on xylose isomerase activity at each xylose concentration.

TABLE 6

| Strain | $V_{max}$ (µmol/mg-protein) | $K_m$ (mM) |
|---|---|---|
| W600W/pRS436GAP-RsXIC1-O | 0.054 ± 0.007 | 13.28 ± 2.02 |
| W600W/pRS436GAP-PiXI-O | 0.078 ± 0.026 | 39.87 ± 7.43 |

As shown in Table 6, the maximum reaction velosity $V_{max}$ for PiXI-0 was about 1.5 times higher than the value for RsXIC1-O, but the $K_m$ value for RsXIC1-O was not more than ⅓ the value for PiXI-O, and thus affinity of the RsXIC1-O for substrate was higher than that of PiXI-O. $K_m$ values for PiXI and CpXI expressed in yeast are reported in Non-patent Literature 1 as being 49.85±2.82 mM for PiXI and 66.01±1.00 mM for CpXI. It can be assumed from this that the $K_m$ value for RsXIC1-O is also lower than the $K_m$ value for CpXI-O.

The yeast S. cerevisiae has no specific transporter for xylose, so uptake of xylose into cells is accomplished non-specifically by hexose transporters. The $K_m$ values of the transporters for xylose (100 mM to 190 mM) are much higher than the $K_m$ values for glucose (1 to 20 mM) (Non-patent Literature 7), so xylose concentrations are expected to be low level in yeast cells. Thus, it is thought that one reason why the xylose utilization ability of the yeast strain with introduced RsXIC1-O is higher than that of yeast strains with other introduced XI is that RsXIC1-O has higher affinity for xylose, and so the reaction progresses more rapidly than with other XIs at low xylose concentrations in the yeast cells.

SEQUENCE LISTING FREE TEXT

SEQ ID NOS: 15 to 44 and 48 to 53: primers
Sequence Listings

The invention claimed is:

1. A nucleic acid selected from any of the following nucleic acids:
   a nucleic acid comprising a nucleotide sequence having at least 85% sequence identity with any of the full-length cDNA sequences of SEQ ID NOS: 1, 3, 5, 7, 9, 11, 13 and the full-length nucleotide sequences complementary thereto; and
   a cDNA coding for a polypeptide having xylose isomerase activity comprising an amino acid sequence having at least 85% sequence identity with any of the full-length amino acid sequences of SEQ ID NOS: 2, 4, 6, 8, 10, 12, and 14.

2. The nucleic acid of claim 1, wherein the nucleic acid comprises a nucleotide sequence having at least 85% sequence identity with any of the full-length cDNA sequences of SEQ ID NOS: 1, 3, 5, 7, 9, 11, 13 and the full-length nucleotide sequences complementary thereto.

3. The nucleic acid of claim 1, wherein the nucleic acid comprises any of the full-length cDNA sequences of SEQ ID NOS: 1, 3, 5, 7, 9, 11, 13 and the full-length nucleotide sequences complementary thereto.

4. The nucleic acid of claim 1, wherein the nucleic acid is a cDNA coding for a polypeptide having xylose isomerase activity comprising an amino acid sequence having at least 85% sequence identity with any of the full-length amino acid sequences of SEQ ID NOS: 2, 4, 6, 8, 10, 12, and 14.

5. The nucleic acid of claim 1, wherein the nucleic acid is a cDNA coding for a polypeptide having xylose isomerase activity comprising any of the full-length amino acid sequences of SEQ ID NOS: 2, 4, 6, 8, 10, 12, and 14.

6. An eukaryotic expression vector comprising the nucleic acid of claim 2.

7. An eukaryotic expression vector comprising the nucleic acid of claim 4.

8. An eukaryotic cell that has been transformed with the eukaryotic expression vector of claim 6.

9. An eukaryotic cell that has been transformed with the eukaryotic expression vector of claim 7.

10. The eukaryotic cell of claim 8, wherein the eukaryotic cell is a yeast.

11. The eukaryotic cell of claim 9, wherein the eukaryotic cell is a yeast.

12. The eukaryotic cell of claim 8, wherein the eukaryotic cell secretorily produces a cellulase.

13. The eukaryotic cell of claim 9, wherein the eukaryotic cell secretorily produces a cellulase.

14. The eukaryotic cell of claim 8, wherein the eukaryotic cell produces one or more enzymes included in an enzyme group of an arabinose metabolic pathway.

15. The eukaryotic cell of claim 9, wherein the eukaryotic cell produces one or more enzymes included in an enzyme group of an arabinose metabolic pathway.

16. The eukaryotic cell of claim 8, wherein the eukaryotic cell is able to convert xylose to any selected from the group consisting of ethanol, lactic acid, acetic acid, 1,3-propanediole, propanol, butanol, succinic acid, ethylene, glycerol, farnesol, geranylgeraniol and squalene.

17. The eukaryotic cell of claim 9, wherein the eukaryotic cell is able to convert xylose to any selected from the group consisting of ethanol, lactic acid, acetic acid, 1,3-propanediole, propanol, butanol, succinic acid, ethylene, glycerol, farnesol, geranylgeraniol and squalene.

18. A method of transforming an eukaryotic cell to express an exogenous xylose isomerase, comprising transforming the eukaryotic cell with the eukaryotic expression vector of claim 6.

19. A method of transforming an eukaryotic cell to express an exogenous xylose isomerase, comprising transforming the eukaryotic cell with the eukaryotic expression vector of claim 7.

* * * * *

SEQUENCE LISTING

```
<160> NUMBER OF SEQ ID NOS: 53

<210> SEQ ID NO 1
<211> LENGTH: 1320
<212> TYPE: DNA
<213> ORGANISM: Reticulitermes speratus

<400> SEQUENCE: 1
atgagtcaga tattcaaaga tattcctgtg atcaaatatg aaggtcctgc gagtaagaat      60
cctttgtcct tcaagtatta tgatgctaac aaggtcattg acggcaaacc catgaaagag     120
catctaagat atgccatggc ttggtggcat aatttgtgtg ccacggggca agatatgttc     180
ggacctggta ccgcggataa gagctttggt tccaagacgg ttggcacaat ggagcatgct     240
cacgcaaaag tggatgcagg cttcgagttc atgtcaaaac ttggggtgga atattttgc      300
```

```
ttccacgatg cagacttggt tcctgaagca gacactttgt cggagaccaa caaacgtttg      360
gatgaaattg ctgaacatat agttgccaaa caaaaagcaa caggaattaa gtgcttgtgg      420
ggaacagcga acttgttttc aacccaagg tttttaaatg gttcagggtc gtctaacagt       480
gctgatgttt atgcttatgc tgcggctcaa attaagaaag cacttgactt gacagtgaaa      540
tttgggggag tgggatatgt gttctggggt ggcagagaag gttatgaaac attgttgaac      600
acggatgtca aattcgaaca ggaaaatatt gccaatttga tgcatcttgc tgtaacgtat      660
ggtcgcagta ttggattcaa aggtgatttc tatattgaac ccaaaccaaa agagccaacg      720
aaacaccagt atgattttga cgccgcgact accattggtt tcattcgtca gtatggtctc      780
gaaaaagatt tcaagctgaa tattgaagca atcatgcca ctttggccgg catacattc        840 caacacgatt gcggatcag tgcgatcaat ggcatgcttg gttctgttga tgcgaacact       900
ggcgatcctt tgcttggctg ggatactgat gaatttccat actctgtgta tgatactacg     960
cttgccatgt atgagatcat caaagctggt ggactgactg gaggattgaa ctttgattcg     1020
aaggtgcgcc gtccttcgta cacgcatgaa gatttgttct atggattcat ccttggcatg    1080
gattcgtttg cgttggggtt gataaaagcg aaagccctca ttgcggatgg ccgtctggac    1140
agtttcgtta agatcgtta cgcgagctat ggatcaggga taggcgcaaa aattcgcgat     1200
cattccgcca ccttggagga attggctgca tatgcactgg cgaaggacac agtggctttg    1260
ccgggaagtg gcagacagga gtacctggaa agcattataa accagattct gtttcagtag    1320
```

<210> SEQ ID NO 2
<211> LENGTH: 439
<212> TYPE: PRT
<213> ORGANISM: Reticulitermes speratus

<400> SEQUENCE: 2

```
Met Ser Gln Ile Phe Lys Asp Ile Pro Val Ile Lys Tyr Glu Gly Pro
  1               5                  10                  15

Ala Ser Lys Asn Pro Leu Ser Phe Lys Tyr Tyr Asp Ala Asn Lys Val
                 20                  25                  30

Ile Asp Gly Lys Pro Met Lys Glu His Leu Arg Tyr Ala Met Ala Trp
             35                  40                  45

Trp His Asn Leu Cys Ala Thr Gly Gln Asp Met Phe Gly Pro Gly Thr
 50                  55                  60

Ala Asp Lys Ser Phe Gly Ser Lys Thr Val Gly Thr Met Glu His Ala
 65                  70                  75                  80

His Ala Lys Val Asp Ala Gly Phe Glu Phe Met Ser Lys Leu Gly Val
                 85                  90                  95

Glu Tyr Phe Cys Phe His Asp Ala Asp Leu Val Pro Glu Ala Asp Thr
                100                 105                 110

Leu Ser Glu Thr Asn Lys Arg Leu Asp Glu Ile Ala Glu His Ile Val
            115                 120                 125

Ala Lys Gln Lys Ala Thr Gly Ile Lys Cys Leu Trp Gly Thr Ala Asn
        130                 135                 140

Leu Phe Ser Asn Pro Arg Phe Leu Asn Gly Ser Gly Ser Ser Asn Ser
145                 150                 155                 160

Ala Asp Val Tyr Ala Tyr Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190
```

Glu Gly Tyr Glu Thr Leu Leu Asn Thr Asp Val Lys Phe Glu Gln Glu
            195                 200                 205

Asn Ile Ala Asn Leu Met His Leu Ala Val Thr Tyr Gly Arg Ser Ile
        210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Thr Ile Gly Phe Ile Arg
                245                 250                 255

Gln Tyr Gly Leu Glu Lys Asp Phe Lys Leu Asn Ile Glu Ala Asn His
            260                 265                 270

Ala Thr Leu Ala Gly His Thr Phe Gln His Asp Leu Arg Ile Ser Ala
        275                 280                 285

Ile Asn Gly Met Leu Gly Ser Val Asp Ala Asn Thr Gly Asp Pro Leu
    290                 295                 300

Leu Gly Trp Asp Thr Asp Glu Phe Pro Tyr Ser Val Tyr Asp Thr Thr
305                 310                 315                 320

Leu Ala Met Tyr Glu Ile Ile Lys Ala Gly Leu Thr Gly Leu
                325                 330                 335

Asn Phe Asp Ser Lys Val Arg Arg Pro Ser Tyr Thr His Glu Asp Leu
            340                 345                 350

Phe Tyr Gly Phe Ile Leu Gly Met Asp Ser Phe Ala Leu Gly Leu Ile
        355                 360                 365

Lys Ala Lys Ala Leu Ile Ala Asp Gly Arg Leu Asp Ser Phe Val Lys
    370                 375                 380

Asp Arg Tyr Ala Ser Tyr Gly Ser Gly Ile Gly Ala Lys Ile Arg Asp
385                 390                 395                 400

His Ser Ala Thr Leu Glu Glu Leu Ala Ala Tyr Ala Leu Ala Lys Asp
                405                 410                 415

Thr Val Ala Leu Pro Gly Ser Gly Arg Gln Glu Tyr Leu Glu Ser Ile
            420                 425                 430

Ile Asn Gln Ile Leu Phe Gln
        435

<210> SEQ ID NO 3
<211> LENGTH: 1320
<212> TYPE: DNA
<213> ORGANISM: Reticulitermes speratus

<400> SEQUENCE: 3
atgagtgcca tatttccaag tgttcccgag attaaatatg aaggtcctgc aagcaaaaac     60
cccttgtcgt tcaagtttta tgaggcaaac agggttattg atggaaagcc catgaaagaa    120
tatttgaaat atgcaatggc ttggtggcat aacttgagca ataatggcac cgacatgttt    180
ggtccaggta ctgcagacaa gagctttggt tctaagactt tgggaacgat ggagcatgct    240
catgcgaaag ttgatgccgg atttgaattt atgaagaaac ttggagttga atacttctgc    300
tttcatgatg cagatttagt tcctgaagga gatacccttg ctgaaacaaa caagcgtttg    360
gatgaaattg cagagcatat tgttaaaaag caggcagaga ctggaatcaa atgtctgtgg    420
ggaacagcaa atctgttttc aaatccaagg tatttgaatg gtgcagggtc aacaaacagt    480
cccgatgtgt atgcctatgc tgctgcccaa atcaagaaag cgcttgattt gacagtgaaa    540
tttgggggag tgggttatgt attctggggt ggcagagaag gttatgaaac attgttaaac    600
acagacgtac agtttgagca agaaaatatt gctaatttga tgcacttggc tgttgattat    660
ggtcggagta ttgggttcaa aggagatttt tatattgaac caaaaccaaa agagccgtca    720

```
aaacaccaat acgatttcga cgcggcaact actatcggct tcattcggca gtatggtctc    780
gacaaggatt tcaagttgaa tattgaagca aatcatgcaa ctttggccgg tcataccttt    840
caacatgatt tgcgcgtcag cgcaatcaac aagatgttgg gctctgttga tgcgaacact    900
ggtgatcctc ttcttggctg ggatacggat gaatttccgt acagtgttta tgacaccacc    960
ctcgcaatgt atgagatttt gaaggctggt ggattgactg ggggtttgaa ttttgattcc   1020
aagaaccgcc gtccttctta tacccacgaa gatatgttct atgggtttat acttggaatg   1080
gatgcgtttg ctttgggact tataaaagca aaagctctta tccaggatgg gcgtctggat   1140
aactttgtta ccgagaagta cgcaagctac aaatcaggga taggtgcaaa gattcgaagt   1200
aaatccacta ccttggtgga attggctgct tacgcagagg ggttgggaaa ggtcgatctt   1260
ccggggagcg gccgtcaaga gtttcttgag agtatattta accagatttt gtttcagtag   1320
```

<210> SEQ ID NO 4
<211> LENGTH: 439
<212> TYPE: PRT
<213> ORGANISM: Reticulitermes speratus

<400> SEQUENCE: 4

```
Met Ser Ala Ile Phe Pro Ser Val Pro Glu Ile Lys Tyr Glu Gly Pro
1               5                   10                  15

Ala Ser Lys Asn Pro Leu Ser Phe Lys Phe Tyr Glu Ala Asn Arg Val
            20                  25                  30

Ile Asp Gly Lys Pro Met Lys Glu Tyr Leu Lys Tyr Ala Met Ala Trp
        35                  40                  45

Trp His Asn Leu Ser Asn Asn Gly Thr Asp Met Phe Gly Pro Gly Thr
    50                  55                  60

Ala Asp Lys Ser Phe Gly Ser Lys Thr Leu Gly Thr Met Glu His Ala
65                  70                  75                  80

His Ala Lys Val Asp Ala Gly Phe Glu Phe Met Lys Lys Leu Gly Val
                85                  90                  95

Glu Tyr Phe Cys Phe His Asp Ala Asp Leu Val Pro Glu Gly Asp Thr
            100                 105                 110

Leu Ala Glu Thr Asn Lys Arg Leu Asp Glu Ile Ala Glu His Ile Val
        115                 120                 125

Lys Lys Gln Ala Glu Thr Gly Ile Lys Cys Leu Trp Gly Thr Ala Asn
    130                 135                 140

Leu Phe Ser Asn Pro Arg Tyr Leu Asn Gly Ala Gly Ser Thr Asn Ser
145                 150                 155                 160

Pro Asp Val Tyr Ala Tyr Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190

Glu Gly Tyr Glu Thr Leu Leu Asn Thr Asp Val Gln Phe Glu Gln Glu
        195                 200                 205

Asn Ile Ala Asn Leu Met His Leu Ala Val Asp Tyr Gly Arg Ser Ile
    210                 215                 220

Gly Phe Lys Gly Asp Phe Tyr Ile Glu Pro Lys Pro Lys Glu Pro Ser
225                 230                 235                 240

Lys His Gln Tyr Asp Phe Asp Ala Ala Thr Thr Ile Gly Phe Ile Arg
                245                 250                 255

Gln Tyr Gly Leu Asp Lys Asp Phe Lys Leu Asn Ile Glu Ala Asn His
            260                 265                 270
```

```
Ala Thr Leu Ala Gly His Thr Phe Gln His Asp Leu Arg Val Ser Ala
        275                 280                 285

Ile Asn Lys Met Leu Gly Ser Val Asp Ala Asn Thr Gly Asp Pro Leu
        290                 295                 300

Leu Gly Trp Asp Thr Asp Glu Phe Pro Tyr Ser Val Tyr Asp Thr Thr
305                 310                 315                 320

Leu Ala Met Tyr Glu Ile Leu Lys Ala Gly Gly Leu Thr Gly Leu
                325                 330                 335

Asn Phe Asp Ser Lys Asn Arg Arg Pro Ser Tyr Thr His Glu Asp Met
                340                 345                 350

Phe Tyr Gly Phe Ile Leu Gly Met Asp Ala Phe Ala Leu Gly Leu Ile
        355                 360                 365

Lys Ala Lys Ala Leu Ile Gln Asp Gly Arg Leu Asp Asn Phe Val Thr
        370                 375                 380

Glu Lys Tyr Ala Ser Tyr Lys Ser Gly Ile Gly Ala Lys Ile Arg Ser
385                 390                 395                 400

Lys Ser Thr Thr Leu Val Glu Leu Ala Ala Tyr Ala Glu Gly Leu Gly
                405                 410                 415

Lys Val Asp Leu Pro Gly Ser Gly Arg Gln Glu Phe Leu Glu Ser Ile
                420                 425                 430

Phe Asn Gln Ile Leu Phe Gln
            435

<210> SEQ ID NO 5
<211> LENGTH: 1323
<212> TYPE: DNA
<213> ORGANISM: Reticulitermes speratus

<400> SEQUENCE: 5
atgagtcagg aaatattcaa aaacattccc caaatcaagt atgaaggtcc cacaagtaaa      60
aatgaactgt cttttaagtt ttatgatgcc aacaaggtca ttgatggaaa acccatgaaa     120
gagtatctga aatatgcgat ggcttggtgg cacaatttgt gtgcaacagg tcaggatatg     180
ttcggttctg ggactgcaga taagcttttt ggtgctaagg aaaaggacac gatggagcat     240
gcccatgcta agttgatgc aggcttcgag ttcatgacaa acttggggt ggaatatttt      300 tgcttcacg atgcggactt ggttccagaa gggaacacat ggcagaaaac caaccagcgt     360
ttggatgaaa ttgcagagca tatagttgcc aaacaaaagg caacagggat taaatgcttg     420
tggggaacgg cgaacttgtt ttctaatccg aggttttga atggtgcagg atcgtctaac     480
agtgctgatg tttatgcata tgctgctgct caaatcaaga aagcacttga tttgaccatc     540
aagtttggag gagttggata tgtattctgg ggtggcagag aaggttatga acattactg     600 aacacagatg tcaagtttga acaggaaaat attgccaatt tgatgcatct tgctgtgaat     660
tatggtcgca gtaagggatt cagaggtgat ttctatattg agcccaaacc aaaagaacca     720
acgaaacacc aatatgattt tgatgctgca actaccattg gcttcattcg gcagtatggt     780
ctggaaaagg atttcaagtt gaatattgaa gcgaatcatg caactttggc agggcatacc     840
ttccagcacg atttgcggat cagtgcgatt aatggcatgc ttggttcagt tgatgcgaat     900
actggcgatc ctttgcttgg ctgggatact gatgaattcc catactctgt gtatgatacc     960
acttttgcca tgtatgagat cctcaaggct ggtggactca ccggaggatt gaactttgat    1020
tcgaaagtac gccgtccttc gtacactctc aaggacatgt ttttaggctt catccttggg    1080
atggatgcat ttgctttggg actgatcaaa gcgaaagctc tcattgcgga tggccgtctg    1140
```

```
gacgattttg tcaaagatcg ttacgcgagc tacggatcgg ggattggtgc aaagattcgc      1200
gatcattctg ccaccttgga ggaattggct gcatatgcgc tggcaaaggg gacagtggag      1260
aaaccaggaa gtggcaaaca ggagtacctg gaaagtattg tgaaccaggt actgtttcag      1320
tga                                                                   1323
```

<210> SEQ ID NO 6
<211> LENGTH: 440
<212> TYPE: PRT
<213> ORGANISM: Reticulitermes speratus

<400> SEQUENCE: 6

```
Met Ser Gln Glu Ile Phe Lys Asn Ile Pro Gln Ile Lys Tyr Glu Gly
1               5                   10                  15

Pro Thr Ser Lys Asn Glu Leu Ser Phe Lys Phe Tyr Asp Ala Asn Lys
            20                  25                  30

Val Ile Asp Gly Lys Pro Met Lys Glu Tyr Leu Lys Tyr Ala Met Ala
        35                  40                  45

Trp Trp His Asn Leu Cys Ala Thr Gly Gln Asp Met Phe Gly Ser Gly
    50                  55                  60

Thr Ala Asp Lys Leu Phe Gly Ala Lys Glu Lys Asp Thr Met Glu His
65                  70                  75                  80

Ala His Ala Lys Val Asp Ala Gly Phe Glu Phe Met Thr Lys Leu Gly
                85                  90                  95

Val Glu Tyr Phe Cys Phe His Asp Ala Asp Leu Val Pro Glu Gly Asn
            100                 105                 110

Thr Leu Ala Glu Thr Asn Gln Arg Leu Asp Glu Ile Ala Glu His Ile
        115                 120                 125

Val Ala Lys Gln Lys Ala Thr Gly Ile Lys Cys Leu Trp Gly Thr Ala
    130                 135                 140

Asn Leu Phe Ser Asn Pro Arg Phe Leu Asn Gly Ala Gly Ser Ser Asn
145                 150                 155                 160

Ser Ala Asp Val Tyr Ala Tyr Ala Ala Ala Gln Ile Lys Lys Ala Leu
                165                 170                 175

Asp Leu Thr Ile Lys Phe Gly Gly Val Gly Tyr Val Phe Trp Gly Gly
            180                 185                 190

Arg Glu Gly Tyr Glu Thr Leu Leu Asn Thr Asp Val Lys Phe Glu Gln
        195                 200                 205

Glu Asn Ile Ala Asn Leu Met His Leu Ala Val Asn Tyr Gly Arg Ser
    210                 215                 220

Lys Gly Phe Arg Gly Asp Phe Tyr Ile Glu Pro Lys Pro Lys Glu Pro
225                 230                 235                 240

Thr Lys His Gln Tyr Asp Phe Asp Ala Ala Thr Thr Ile Gly Phe Ile
                245                 250                 255

Arg Gln Tyr Gly Leu Glu Lys Asp Phe Lys Leu Asn Ile Glu Ala Asn
            260                 265                 270

His Ala Thr Leu Ala Gly His Thr Phe Gln His Asp Leu Arg Ile Ser
        275                 280                 285

Ala Ile Asn Gly Met Leu Gly Ser Val Asp Ala Asn Thr Gly Asp Pro
    290                 295                 300

Leu Leu Gly Trp Asp Thr Asp Glu Phe Pro Tyr Ser Val Tyr Asp Thr
305                 310                 315                 320

Thr Phe Ala Met Tyr Glu Ile Leu Lys Ala Gly Gly Leu Thr Gly Gly
                325                 330                 335
```

```
Leu Asn Phe Asp Ser Lys Val Arg Arg Pro Ser Tyr Thr Leu Lys Asp
            340                 345                 350

Met Phe Leu Gly Phe Ile Leu Gly Met Asp Ala Phe Ala Leu Gly Leu
        355                 360                 365

Ile Lys Ala Lys Ala Leu Ile Ala Asp Gly Arg Leu Asp Asp Phe Val
370                 375                 380

Lys Asp Arg Tyr Ala Ser Tyr Gly Ser Gly Ile Gly Ala Lys Ile Arg
385                 390                 395                 400

Asp His Ser Ala Thr Leu Glu Glu Leu Ala Ala Tyr Ala Leu Ala Lys
                405                 410                 415

Gly Thr Val Glu Lys Pro Gly Ser Gly Lys Gln Glu Tyr Leu Glu Ser
            420                 425                 430

Ile Val Asn Gln Val Leu Phe Gln
            435                 440

<210> SEQ ID NO 7
<211> LENGTH: 1323
<212> TYPE: DNA
<213> ORGANISM: Reticulitermes speratus

<400> SEQUENCE: 7
atgtccaccg aaatattccc aggaatcaag caaattgtct atgagggacc cgcaagcaaa      60
aatccgctgg cttttaagtt ttatgatgag aaaaaacttg ttggtggaaa accaatgaaa     120
gaatggctga gatttgcaat ggcgtggtgg cataaccttt gtgcagttgg aggtgacatg     180
tttggttcgg gaacaatgga taagagcttt ggagcgaaga ctactggaac aatggagcat     240
gcaaaagcga agttgatgc gggatttgag ttcatgacaa agttgggtgt tgaatatttc     300
tgcttccatg atgcggatct tgttcctgat ggaaatacgt tggctgagac caacaaaaat     360
ctggatgaga ttggggatta tattgttgcg aagcaaaagg catctggaat taaatgtctt     420
tggggaactg ccaacttgtt ttcacatcca aggtacgcaa atggttcggg ctcttccaac     480
tgcgcggatg tttacgcgta tgcagctgct caaataaaga aagcacttga tttaactgtt     540
cgatttggcg gagtgggata tgtgttttgg ggtgggagag agggatatga aacattatta     600
aatactgatg taaagtttga caagaaaaat attgcaaatc tgatgaaact agctgttact     660
tatggtcgga gtattggttt caaaggtgat ttttatatag aacccaagcc taaagaacca     720
acaaagcatc aatatgactt tgatgctgcg acaaccattg ggttcattcg tcagtatggt     780
ttgcaaaatg acttcaaact caacatcgag gcaaatcatg ccactcttgc tggccacaca     840
tttcagcatg acttgcgtat cagtgcaatc aatggaatgc tcggatctgt ggatgctaat     900
actggtgacc ctcttcttgg ctgggatact gatgagtttc catacagtgt atatgataca     960
actcttgcta tgtatgaaat catcaaagct ggtggcttga caggtggtct gaactttgac    1020
tcaaagatcc ggcgtccgtc gtacactcac gaagatttgt ttctgggttt catactaggg    1080
atggacgcct ttgcactggg actcatcaaa gctgatgcac taatcaagga tgggcgtctt    1140
gacggcttcg tcactgaccg ttatggaagt acaaatccg gaatcggtgc aaggattcga    1200
gatcattctg caacactcgt ggagctggcg gagtatgcag aaaaactggg taaagtggaa    1260
agggctggga gtgggaagca ggagtatctc gaaagtgtgt taatcaaat tctgtttcag    1320 taa                                                                  1323

<210> SEQ ID NO 8
<211> LENGTH: 440
```

<212> TYPE: PRT
<213> ORGANISM: Reticulitermes speratus

<400> SEQUENCE: 8

Met Ser Thr Glu Ile Phe Pro Gly Ile Lys Gln Ile Val Tyr Glu Gly
1               5                   10                  15

Pro Ala Ser Lys Asn Pro Leu Ala Phe Lys Phe Tyr Asp Glu Lys Lys
            20                  25                  30

Leu Val Gly Gly Lys Pro Met Lys Glu Trp Leu Arg Phe Ala Met Ala
        35                  40                  45

Trp Trp His Asn Leu Cys Ala Val Gly Gly Asp Met Phe Gly Ser Gly
50                  55                  60

Thr Met Asp Lys Ser Phe Gly Ala Lys Thr Thr Gly Thr Met Glu His
65                  70                  75                  80

Ala Lys Ala Lys Val Asp Ala Gly Phe Glu Phe Met Thr Lys Leu Gly
                85                  90                  95

Val Glu Tyr Phe Cys Phe His Asp Ala Asp Leu Val Pro Asp Gly Asn
            100                 105                 110

Thr Leu Ala Glu Thr Asn Lys Asn Leu Asp Glu Ile Gly Asp Tyr Ile
        115                 120                 125

Val Ala Lys Gln Lys Ala Ser Gly Ile Lys Cys Leu Trp Gly Thr Ala
130                 135                 140

Asn Leu Phe Ser His Pro Arg Tyr Ala Asn Gly Ser Gly Ser Ser Asn
145                 150                 155                 160

Cys Ala Asp Val Tyr Ala Tyr Ala Ala Gln Ile Lys Lys Ala Leu
                165                 170                 175

Asp Leu Thr Val Arg Phe Gly Gly Val Gly Tyr Val Phe Trp Gly Gly
            180                 185                 190

Arg Glu Gly Tyr Glu Thr Leu Leu Asn Thr Asp Val Lys Phe Glu Gln
        195                 200                 205

Glu Asn Ile Ala Asn Leu Met Lys Leu Ala Val Thr Tyr Gly Arg Ser
210                 215                 220

Ile Gly Phe Lys Gly Asp Phe Tyr Ile Glu Pro Lys Pro Lys Glu Pro
225                 230                 235                 240

Thr Lys His Gln Tyr Asp Phe Asp Ala Ala Thr Thr Ile Gly Phe Ile
                245                 250                 255

Arg Gln Tyr Gly Leu Gln Asn Asp Phe Lys Leu Asn Ile Glu Ala Asn
            260                 265                 270

His Ala Thr Leu Ala Gly His Thr Phe Gln His Asp Leu Arg Ile Ser
        275                 280                 285

Ala Ile Asn Gly Met Leu Gly Ser Val Asp Ala Asn Thr Gly Asp Pro
290                 295                 300

Leu Leu Gly Trp Asp Thr Asp Glu Phe Pro Tyr Ser Val Tyr Asp Thr
305                 310                 315                 320

Thr Leu Ala Met Tyr Glu Ile Ile Lys Ala Gly Gly Leu Thr Gly Gly
                325                 330                 335

Leu Asn Phe Asp Ser Lys Ile Arg Arg Pro Ser Tyr Thr His Glu Asp
            340                 345                 350

Leu Phe Leu Gly Phe Ile Leu Gly Met Asp Ala Phe Ala Leu Gly Leu
        355                 360                 365

Ile Lys Ala Asp Ala Leu Ile Lys Asp Gly Arg Leu Asp Gly Phe Val
370                 375                 380

Thr Asp Arg Tyr Gly Ser Tyr Lys Ser Gly Ile Gly Ala Arg Ile Arg
385                 390                 395                 400

Asp His Ser Ala Thr Leu Val Glu Leu Ala Glu Tyr Ala Glu Lys Leu
             405                 410                 415

Gly Lys Val Glu Arg Ala Gly Ser Gly Lys Gln Glu Tyr Leu Glu Ser
         420                 425                 430

Val Phe Asn Gln Ile Leu Phe Gln
         435                 440

<210> SEQ ID NO 9
<211> LENGTH: 1320
<212> TYPE: DNA
<213> ORGANISM: Mastotermes darwiniensis

<400> SEQUENCE: 9

```
atgtctcacg aatactttcc aggcatcagc aagatccaat ttgaaggcaa gaatagccta      60
aatccattgg cgtttcgtta ttatcaacca gacaaggttg tttatggtcg taagatgaag     120
gattggtttg agttttcagt tgcttggtgg cataccttct gcggtgaagg tggtgatcca     180
tttggcccag gcacgaaagc atttccatgg aatcaaggag aactttcagc gattgaactt     240
gggaaacaga agttgatgc agcttttgaa ttgatgacga aactgagcat tgaatatttc      300
tgcttccatg atgttgacct tgttagtgaa ggttcttcaa ttgaagaata tgaatcgaat     360
cttaaagcag ttgttgcata catcaaagag aaacaaactg cgacggggat caaatgcctt     420
tggggcactg ctaatgtttt tggtcataag aggtatacta atggtgcagc aaccaatccc     480
gattttgatg ttgttactcg tgtggcagtg caactgaaga atgcaattga tgcaacgatt     540
gaactcggag gtgagaatta tgttttctgg ggtggtcgtg aaggatatta ctcacttctt     600
aatacgcaaa tgggtcgaga aaaggaacat ttggccataa tattaacaaa ggctcgcgat     660
tatgcaaggt caaaggtttt caagggaaca tttttgatcg aaccaaaacc atgtgaaccg     720
acgaaacatc aatatgatac tgatgcagag acagtgattg gtttccttcg tgctcatggt     780
cttgacaaag acttcaaatt gaatattgaa gtgaaccatg caacacttgc aggccatacg     840
tttgaacatg aattacaatg tgcagctgat gcaggaatgc ttgggtcaat tgatgcaaat     900
cgaggagatg cccaaaacgg ttgggatact gaccaattcc cagttgatgc atatgaacta     960
actcaagcgc tgcttgttat cttgcgagct ggaggacttc aaggtggtgg gactaacttt    1020
gatgctaaaa ctcgtcgaag ctcaactgat cttgaagaca ttttcattgc acatatctct    1080
ggaatggatg cttttgctcg cgctttagaa gcggcagctg caattcttga gcgctctcca    1140
tatgttaagt tgcttactga gcgttacgca tcatttgata gtggaccagg caaggagttt    1200
gaggaaggta acttctctct tgaggatctt gttgcaattg cgaagtcaaa gaatgaagaa    1260
ccaaagcaaa ttagtggaaa acaagagctt tatgagctga tagtgacgat gttccaataa    1320
```

<210> SEQ ID NO 10
<211> LENGTH: 439
<212> TYPE: PRT
<213> ORGANISM: Mastotermes darwiniensis

<400> SEQUENCE: 10

Met Ser His Glu Tyr Phe Pro Gly Ile Ser Lys Ile Gln Phe Glu Gly
1               5                   10                  15

Lys Asn Ser Leu Asn Pro Leu Ala Phe Arg Tyr Tyr Gln Pro Asp Lys
            20                  25                  30

Val Val Tyr Gly Arg Lys Met Lys Asp Trp Phe Glu Phe Ser Val Ala
        35                  40                  45

Trp Trp His Thr Phe Cys Gly Glu Gly Gly Asp Pro Phe Gly Pro Gly
 50                  55                  60

Thr Lys Ala Phe Pro Trp Asn Gln Gly Glu Leu Ser Ala Ile Glu Leu
 65                  70                  75                  80

Gly Lys Gln Lys Val Asp Ala Ala Phe Glu Leu Met Thr Lys Leu Ser
                 85                  90                  95

Ile Glu Tyr Phe Cys Phe His Asp Val Asp Leu Val Ser Glu Gly Ser
            100                 105                 110

Ser Ile Glu Glu Tyr Glu Ser Asn Leu Lys Ala Val Ala Tyr Ile
        115                 120                 125

Lys Glu Lys Gln Thr Ala Thr Gly Ile Lys Cys Leu Trp Gly Thr Ala
130                 135                 140

Asn Val Phe Gly His Lys Arg Tyr Thr Asn Gly Ala Ala Thr Asn Pro
145                 150                 155                 160

Asp Phe Asp Val Val Thr Arg Val Ala Val Gln Leu Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Tyr Ser Leu Leu Asn Thr Gln Met Gly Arg Glu Lys
        195                 200                 205

Glu His Leu Ala Ile Ile Leu Thr Lys Ala Arg Asp Tyr Ala Arg Ser
    210                 215                 220

Lys Gly Phe Lys Gly Thr Phe Leu Ile Glu Pro Lys Pro Cys Glu Pro
225                 230                 235                 240

Thr Lys His Gln Tyr Asp Thr Asp Ala Glu Thr Val Ile Gly Phe Leu
                245                 250                 255

Arg Ala His Gly Leu Asp Lys Asp Phe Lys Leu Asn Ile Glu Val Asn
            260                 265                 270

His Ala Thr Leu Ala Gly His Thr Phe Glu His Glu Leu Gln Cys Ala
        275                 280                 285

Ala Asp Ala Gly Met Leu Gly Ser Ile Asp Ala Asn Arg Gly Asp Ala
    290                 295                 300

Gln Asn Gly Trp Asp Thr Asp Gln Phe Pro Val Asp Ala Tyr Glu Leu
305                 310                 315                 320

Thr Gln Ala Leu Leu Val Ile Leu Arg Ala Gly Gly Leu Gln Gly Gly
                325                 330                 335

Gly Thr Asn Phe Asp Ala Lys Thr Arg Arg Ser Ser Thr Asp Leu Glu
            340                 345                 350

Asp Ile Phe Ile Ala His Ile Ser Gly Met Asp Ala Phe Ala Arg Ala
        355                 360                 365

Leu Glu Ala Ala Ala Ile Leu Glu Arg Ser Pro Tyr Val Lys Leu
    370                 375                 380

Leu Thr Glu Arg Tyr Ala Ser Phe Asp Ser Gly Pro Gly Lys Glu Phe
385                 390                 395                 400

Glu Glu Gly Lys Leu Ser Leu Glu Asp Leu Val Ala Ile Ala Lys Ser
                405                 410                 415

Lys Asn Glu Glu Pro Lys Gln Ile Ser Gly Lys Gln Glu Leu Tyr Glu
            420                 425                 430

Leu Ile Val Thr Met Phe Gln
        435

<210> SEQ ID NO 11
<211> LENGTH: 1320
<212> TYPE: DNA

<213> ORGANISM: Mastotermes darwiniensis

<400> SEQUENCE: 11

```
atgtctggcg aatactttcc aggtattagc aagatacagt ttgaaggcaa ggagagtttg      60
aatccattag cgtttcatta ttatcaacca gagaaggttg tttatgggcg aagatgaag      120
gattggttta aattttcggt tgcttggtgg catactttct gcggtgatgg tggtgatcca     180
tttggcccag gcacgaaaac atttccatgg aatcaaggaa aaggttcagc ggtcgaactt     240
ggaaaacaaa aagttgatgc agcttttgaa ttgatgacga aattgagcat tgaatatttt    300
tgcttccatg atatcgatct tgttagtgaa ggttcatcaa ttgaagaata tgaatctaat    360
cttaaagcag ttgttgcata catcaaagag aaacaggcag cgacgggaat caaatgcctt    420
tggggcactg ctaatgtttt tggtcacaag cgatatacta cggtgcagc aaccaaccca      480
gattttgatg ttgttactcg tgtagcagta caactgaaga atgcaattga tgcaacgatt    540
gaactgggag gtgagaatta tgttttctgg ggtggtcgtg aaggatatta cacacttctt    600
aatacgcaaa tgggccgaga aaggaacat ttagcaacaa tattaacgaa ggctcgtgat      660
tatgcaaggt caaaaggttt caagggaaca ttttgattg aaccgaaacc ctgcgaacca      720
acgaaacatc aatatgacgc agatgcggag acagtgattg ggttccttcg tgctcatggt    780
cttgacaaag acttcaaatt gaatatcgaa gtgaaccatg caaccccttgc agggcatacg    840
tttgaacatg agctgcaatg tgcagctgat gcaggaatgc ttgggtcaat tgatgcgaat    900
cgcggagatg ctcaaaacgg ttgggatact gatcaattcc cagtggatgc atatgaactc    960
actcaagcaa tgcttgttat cttgcgagct ggaggacttc aaggtggtgg gactaatttt   1020
gatgctaaga ctcgtcgatc ctcaactgat cttgaagata ttttcattgc acatatttg    1080
ggaatggatg cttttgctcg tgctttggaa gccgctgccg caattcttga gcgctctccc   1140
tatcttaagt tggttactga acgttatgca tcatttgata gtggaccagg taaagagttt   1200
gaggaaggta aactgtcact tgaagatctt gttgctcttg ctaagacgaa taatgcagaa   1260
ccaaagcaaa ttagtggcaa acaagagctt tatgagctca tagtgacgac gttccaatga   1320
```

<210> SEQ ID NO 12
<211> LENGTH: 439
<212> TYPE: PRT
<213> ORGANISM: Mastotermes darwiniensis

<400> SEQUENCE: 12

```
Met Ser Gly Glu Tyr Phe Pro Gly Ile Ser Lys Ile Gln Phe Glu Gly
1               5                  10                  15

Lys Glu Ser Leu Asn Pro Leu Ala Phe His Tyr Tyr Gln Pro Glu Lys
            20                  25                  30

Val Val Tyr Gly Arg Lys Met Lys Asp Trp Phe Lys Phe Ser Val Ala
        35                  40                  45

Trp Trp His Thr Phe Cys Gly Asp Gly Asp Pro Phe Gly Pro Gly
    50                  55                  60

Thr Lys Thr Phe Pro Trp Asn Gln Gly Lys Gly Ser Ala Val Glu Leu
65                  70                  75                  80

Gly Lys Gln Lys Val Asp Ala Ala Phe Glu Leu Met Thr Lys Leu Ser
                85                  90                  95

Ile Glu Tyr Phe Cys Phe His Asp Ile Asp Leu Val Ser Glu Gly Ser
            100                 105                 110

Ser Ile Glu Glu Tyr Glu Ser Asn Leu Lys Ala Val Val Ala Tyr Ile
        115                 120                 125
```

```
Lys Glu Lys Gln Ala Ala Thr Gly Ile Lys Cys Leu Trp Gly Thr Ala
        130                 135                 140
Asn Val Phe Gly His Lys Arg Tyr Thr Asn Gly Ala Ala Thr Asn Pro
145                 150                 155                 160
Asp Phe Asp Val Val Thr Arg Val Ala Val Gln Leu Lys Asn Ala Ile
                165                 170                 175
Asp Ala Thr Ile Glu Leu Gly Gly Glu Asn Tyr Val Phe Trp Gly Gly
            180                 185                 190
Arg Glu Gly Tyr Tyr Thr Leu Leu Asn Thr Gln Met Gly Arg Glu Lys
        195                 200                 205
Glu His Leu Ala Thr Ile Leu Thr Lys Ala Arg Asp Tyr Ala Arg Ser
    210                 215                 220
Lys Gly Phe Lys Gly Thr Phe Leu Ile Glu Pro Lys Pro Cys Glu Pro
225                 230                 235                 240
Thr Lys His Gln Tyr Asp Ala Asp Ala Glu Thr Val Ile Gly Phe Leu
                245                 250                 255
Arg Ala His Gly Leu Asp Lys Asp Phe Lys Leu Asn Ile Glu Val Asn
            260                 265                 270
His Ala Thr Leu Ala Gly His Thr Phe Glu His Glu Leu Gln Cys Ala
        275                 280                 285
Ala Asp Ala Gly Met Leu Gly Ser Ile Asp Ala Asn Arg Gly Asp Ala
290                 295                 300
Gln Asn Gly Trp Asp Thr Asp Gln Phe Pro Val Asp Ala Tyr Glu Leu
305                 310                 315                 320
Thr Gln Ala Met Leu Val Ile Leu Arg Ala Gly Gly Leu Gln Gly Gly
                325                 330                 335
Gly Thr Asn Phe Asp Ala Lys Thr Arg Arg Ser Ser Thr Asp Leu Glu
            340                 345                 350
Asp Ile Phe Ile Ala His Ile Leu Gly Met Asp Ala Phe Ala Arg Ala
        355                 360                 365
Leu Glu Ala Ala Ala Ile Leu Glu Arg Ser Pro Tyr Leu Lys Leu
    370                 375                 380
Val Thr Glu Arg Tyr Ala Ser Phe Asp Ser Gly Pro Gly Lys Glu Phe
385                 390                 395                 400
Glu Glu Gly Lys Leu Ser Leu Glu Asp Leu Val Ala Leu Ala Lys Thr
                405                 410                 415
Asn Asn Ala Glu Pro Lys Gln Ile Ser Gly Lys Gln Glu Leu Tyr Glu
            420                 425                 430
Leu Ile Val Thr Thr Phe Gln
        435

<210> SEQ ID NO 13
<211> LENGTH: 1320
<212> TYPE: DNA
<213> ORGANISM: Mastotermes darwiniensis

<400> SEQUENCE: 13
atgtctcgcg aatactttcc aggtattggc aagattgctt ttgaaggtaa ggagagcaag    60
aacccttggg cctttcggta ttaccagcct gagaaggaag tttatgggcg aaagatgaaa   120
gattggttta agtttgctgc ttgttggtgg cattcattta ctggtgatgg tggtgatccc   180
tttgggccag ggactaaggt ctatccttgg actcaaggaa ctactgatgc tgttgaactt   240
ggtaagcaaa aggcggatgc tgcttttgaa tttatgacta aggtggggat tgaatatttc   300
```

```
tgttttcatg atattgacct tgttgctgaa ggaaattcca ttgaagaata tgaagcaaat    360
cttaaggcag tagtggctca tatcaagcaa aaacaggctg aaactggcat taaatgtctt    420
tggggaactg caaatgtttt tggccataag agatatacaa atggtgctgc gacgagccct    480
gactttgatt tgttgctcg agttgctgtt cagttaaaga atgcaattga tgcaacgatt    540
gaacttggtg gtgaaaatta tgttttctgg ggtggccgtg aaggatatta cactttgttg    600
aatactcaaa tgggtcgtga gaaatctcat cttgctacga tgctgacaaa ggctcgagat    660
tatgcaaggt cgaaaggctt taaggaaca ttcttcatcg agcctaagcc atgtgagccg    720
acgaagcatc aatacgatgc tgatgttgaa actgtaattg gattccttag agctcatggt    780
cttgacaagg actttaagtt aaatattgaa gtgaatcatg cagtccttgc tggccatact    840
tttgaacatg aattgcaatg tgcggtagat gctggattgc ttggatcaat tgatgctaat    900
cgtggtgact atcagaacgg ttgggatacc gatcagttcc ctgttgatgc ttatgagttg    960
acccaggcat tgcttgttat tcttcaaggt ggtggacttc aaggtggtgg tacgaacttt   1020
gacgcaaaaa ctcgaaggag ctcaactgat cctcaagacc tcttcattgc acatatctgt   1080
ggaatggatg catttgctcg tgcactagag gccgcggcag caatccttga gaaatcgcct   1140
tacaagaaga tgctcaccga tcgttatgcg tcctttgatg ctgggtctgg aaaagagttc   1200
gaggaaggca aactgtcttt ggaggacctc gttgcttatg caaagtcgaa gaacactgaa   1260
ccagagcaaa gaagtggtca acaagagctc tatgagctaa tcgtaacaat gtaccagtga   1320
```

```
<210> SEQ ID NO 14
<211> LENGTH: 439
<212> TYPE: PRT
<213> ORGANISM: Mastotermes darwiniensis

<400> SEQUENCE: 14

Met Ser Arg Glu Tyr Phe Pro Gly Ile Gly Lys Ile Ala Phe Glu Gly
1               5                   10                  15

Lys Glu Ser Lys Asn Pro Leu Ala Phe Arg Tyr Gln Pro Glu Lys
            20                  25                  30

Glu Val Tyr Gly Arg Lys Met Lys Asp Trp Phe Lys Phe Ala Ala Cys
        35                  40                  45

Trp Trp His Ser Phe Thr Gly Asp Gly Gly Asp Pro Phe Gly Pro Gly
    50                  55                  60

Thr Lys Val Tyr Pro Trp Thr Gln Gly Thr Thr Asp Ala Val Glu Leu
65                  70                  75                  80

Gly Lys Gln Lys Ala Asp Ala Ala Phe Glu Phe Met Thr Lys Val Gly
                85                  90                  95

Ile Glu Tyr Phe Cys Phe His Asp Ile Asp Leu Val Ala Glu Gly Asn
            100                 105                 110

Ser Ile Glu Glu Tyr Glu Ala Asn Leu Lys Ala Val Ala His Ile
        115                 120                 125

Lys Gln Lys Gln Ala Glu Thr Gly Ile Lys Cys Leu Trp Gly Thr Ala
    130                 135                 140

Asn Val Phe Gly His Lys Arg Tyr Thr Asn Gly Ala Ala Thr Ser Pro
145                 150                 155                 160

Asp Phe Asp Val Val Ala Arg Val Ala Val Gln Leu Lys Asn Ala Ile
                165                 170                 175

Asp Ala Thr Ile Glu Leu Gly Gly Glu Asn Tyr Val Phe Trp Gly Gly
            180                 185                 190

Arg Glu Gly Tyr Tyr Thr Leu Leu Asn Thr Gln Met Gly Arg Glu Lys
```

```
                195                 200                 205
Ser His Leu Ala Thr Met Leu Thr Lys Ala Arg Asp Tyr Ala Arg Ser
    210                 215                 220

Lys Gly Phe Lys Gly Thr Phe Phe Ile Glu Pro Lys Pro Cys Glu Pro
225                 230                 235                 240

Thr Lys His Gln Tyr Asp Ala Asp Val Glu Thr Val Ile Gly Phe Leu
                245                 250                 255

Arg Ala His Gly Leu Asp Lys Asp Phe Lys Leu Asn Ile Glu Val Asn
            260                 265                 270

His Ala Val Leu Ala Gly His Thr Phe Glu His Glu Leu Gln Cys Ala
        275                 280                 285

Val Asp Ala Gly Leu Leu Gly Ser Ile Asp Ala Asn Arg Gly Asp Tyr
    290                 295                 300

Gln Asn Gly Trp Asp Thr Asp Gln Phe Pro Val Asp Ala Tyr Glu Leu
305                 310                 315                 320

Thr Gln Ala Leu Leu Val Ile Leu Gln Gly Gly Leu Gln Gly Gly
                325                 330                 335

Gly Thr Asn Phe Asp Ala Lys Thr Arg Arg Ser Ser Thr Asp Pro Gln
            340                 345                 350

Asp Leu Phe Ile Ala His Ile Cys Gly Met Asp Ala Phe Ala Arg Ala
        355                 360                 365

Leu Glu Ala Ala Ala Ile Leu Glu Lys Ser Pro Tyr Lys Lys Met
    370                 375                 380

Leu Thr Asp Arg Tyr Ala Ser Phe Asp Ala Gly Ser Gly Lys Glu Phe
385                 390                 395                 400

Glu Glu Gly Lys Leu Ser Leu Glu Asp Leu Val Ala Tyr Ala Lys Ser
                405                 410                 415

Lys Asn Thr Glu Pro Glu Gln Arg Ser Gly Gln Glu Leu Tyr Glu
            420                 425                 430

Leu Ile Val Thr Met Tyr Gln
            435

<210> SEQ ID NO 15
<211> LENGTH: 50
<212> TYPE: DNA
<213> ORGANISM: Artificial Sequence
<220> FEATURE:
<223> OTHER INFORMATION: Synthetic Construct - primer

<400> SEQUENCE: 15
taaacacaca taaacaaaca aacccctcga gttaattaaa ttaatccccc              50

<210> SEQ ID NO 16
<211> LENGTH: 47
<212> TYPE: DNA
<213> ORGANISM: Artificial Sequence
<220> FEATURE:
<223> OTHER INFORMATION: Synthetic Construct - primer

<400> SEQUENCE: 16
ttactcctcg agggccacat aggccgagct cttttttttt tttttt                   47

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct - primer
<220> FEATURE:
```

<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 17
tggggnggnm gngarggnta y                                   21

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct - primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 18
nggraaytgr tcngtrtccc a                                   21

<210> SEQ ID NO 19
<211> LENGTH: 17
<212> TYPE: DNA
<213> ORGANISM: Artificial Sequence
<220> FEATURE:
<223> OTHER INFORMATION: Synthetic Construct - primer

<400> SEQUENCE: 19
gtaaaacgac ggccagt                                        17

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct - primer

<400> SEQUENCE: 20
caggaaacag ctatgaccat                                     20

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct - primer

<400> SEQUENCE: 21
tcgcttcaat attcagtttg aaatc                               25

<210> SEQ ID NO 22
<211> LENGTH: 25

```
<212> TYPE: DNA
<213> ORGANISM: Artificial Sequence
<220> FEATURE:
<223> OTHER INFORMATION: Synthetic Construct - primer

<400> SEQUENCE: 22
atcatgcaac tttggctggt catac                                           25

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct - primer

<400> SEQUENCE: 23
tcgcttcaat attcagttta aaatc                                           25

<210> SEQ ID NO 24
<211> LENGTH: 34
<212> TYPE: DNA
<213> ORGANISM: Artificial Sequence
<220> FEATURE:
<223> OTHER INFORMATION: Synthetic Construct - primer

<400> SEQUENCE: 24
accaatactc cgaccataag taacagctag tttc                                 34

<210> SEQ ID NO 25
<211> LENGTH: 72
<212> TYPE: DNA
<213> ORGANISM: Artificial Sequence
<220> FEATURE:
<223> OTHER INFORMATION: Synthetic Construct - primer

<400> SEQUENCE: 25
ataaacaaac aaaccgcgga aaatgagtca gatattcaaa gatattcctg tgatcaaata     60
tgaaggtcct gc                                                         72

<210> SEQ ID NO 26
<211> LENGTH: 66
<212> TYPE: DNA
<213> ORGANISM: Artificial Sequence
<220> FEATURE:
<223> OTHER INFORMATION: Synthetic Construct - primer

<400> SEQUENCE: 26
tgatgcggcc ctcgagctac tgaaacaaaa tctggttaaa tatactctca agaaactctt     60
gacggc                                                                66

<210> SEQ ID NO 27
<211> LENGTH: 72
<212> TYPE: DNA
<213> ORGANISM: Artificial Sequence
<220> FEATURE:
<223> OTHER INFORMATION: Synthetic Construct - primer

<400> SEQUENCE: 27
ataaacaaac aaaccgcgga aaatgagtca ggaaatattc aaaaacattc cccaaatcaa     60
atatgagggt cc                                                         72

<210> SEQ ID NO 28
<211> LENGTH: 22
<212> TYPE: DNA
```

<213> ORGANISM: Artificial Sequence
<220> FEATURE:
<223> OTHER INFORMATION: Synthetic Construct - primer

<400> SEQUENCE: 28
actcttgctg gccacacatt tc					22

<210> SEQ ID NO 29
<211> LENGTH: 52
<212> TYPE: DNA
<213> ORGANISM: Artificial Sequence
<220> FEATURE:
<223> OTHER INFORMATION: Synthetic Construct - primer

<400> SEQUENCE: 29
ataaacaaac aaaccgcgga aaatgagtca gatattcaaa gatattcctg tg					52

<210> SEQ ID NO 30
<211> LENGTH: 49
<212> TYPE: DNA
<213> ORGANISM: Artificial Sequence
<220> FEATURE:
<223> OTHER INFORMATION: Synthetic Construct - primer

<400> SEQUENCE: 30
tgatgcggcc ctcgagctac tgaaacagaa tctggtttat aatgctttc					49

<210> SEQ ID NO 31
<211> LENGTH: 52
<212> TYPE: DNA
<213> ORGANISM: Artificial Sequence
<220> FEATURE:
<223> OTHER INFORMATION: Synthetic Construct - primer

<400> SEQUENCE: 31
ataaacaaac aaaccgcgga aaatgagtgc catatttcca agtgttcccg ag					52

<210> SEQ ID NO 32
<211> LENGTH: 49
<212> TYPE: DNA
<213> ORGANISM: Artificial Sequence
<220> FEATURE:
<223> OTHER INFORMATION: Synthetic Construct - primer

<400> SEQUENCE: 32
tgatgcggcc ctcgagctac tgaaacaaaa tctggttaaa tatactctc					49

<210> SEQ ID NO 33
<211> LENGTH: 52
<212> TYPE: DNA
<213> ORGANISM: Artificial Sequence
<220> FEATURE:
<223> OTHER INFORMATION: Synthetic Construct - primer

<400> SEQUENCE: 33
ataaacaaac aaaccgcgga aaatgagtca ggaaatattc aaaaacattc cc					52

<210> SEQ ID NO 34
<211> LENGTH: 49
<212> TYPE: DNA
<213> ORGANISM: Artificial Sequence
<220> FEATURE:
<223> OTHER INFORMATION: Synthetic Construct - primer

<400> SEQUENCE: 34
tgatgcggcc ctcgagtcac tgaaacagta cctggttcac aatactttc					49

<210> SEQ ID NO 35
<211> LENGTH: 59
<212> TYPE: DNA
<213> ORGANISM: Artificial Sequence
<220> FEATURE:
<223> OTHER INFORMATION: Synthetic Construct - primer

<400> SEQUENCE: 35
ataaacaaac aaaccgcgga aaatgtccac cgaaatattc ccaggaatca agcaaattc      59

<210> SEQ ID NO 36
<211> LENGTH: 59
<212> TYPE: DNA
<213> ORGANISM: Artificial Sequence
<220> FEATURE:
<223> OTHER INFORMATION: Synthetic Construct - primer

<400> SEQUENCE: 36
tgatgcggcc ctcgagttac tgaaacagaa tttgattaaa cacactttcg agatactcc      59

<210> SEQ ID NO 37
<211> LENGTH: 22
<212> TYPE: DNA
<213> ORGANISM: Artificial Sequence
<220> FEATURE:
<223> OTHER INFORMATION: Synthetic Construct - primer

<400> SEQUENCE: 37
ccagttccct gaaattattc cc                                              22

<210> SEQ ID NO 38
<211> LENGTH: 22
<212> TYPE: DNA
<213> ORGANISM: Artificial Sequence
<220> FEATURE:
<223> OTHER INFORMATION: Synthetic Construct - primer

<400> SEQUENCE: 38
cctagacttc aggttgtcta ac                                              22

<210> SEQ ID NO 39
<211> LENGTH: 45
<212> TYPE: DNA
<213> ORGANISM: Artificial Sequence
<220> FEATURE:
<223> OTHER INFORMATION: Synthetic Construct - primer

<400> SEQUENCE: 39
ataaacaaac aaaccgcgga aaatgtctca cgaatacttt ccagg                     45

<210> SEQ ID NO 40
<211> LENGTH: 38
<212> TYPE: DNA
<213> ORGANISM: Artificial Sequence
<220> FEATURE:
<223> OTHER INFORMATION: Synthetic Construct - primer

<400> SEQUENCE: 40
tgatgcggcc ctcgagttat tggaacatcg tcactatc                             38

<210> SEQ ID NO 41
<211> LENGTH: 45
<212> TYPE: DNA
<213> ORGANISM: Artificial Sequence
<220> FEATURE:

<223> OTHER INFORMATION: Synthetic Construct - primer

<400> SEQUENCE: 41
ataaacaaac aaaccgcgga aaatgtctgg cgaatacttt ccagg        45

<210> SEQ ID NO 42
<211> LENGTH: 38
<212> TYPE: DNA
<213> ORGANISM: Artificial Sequence
<220> FEATURE:
<223> OTHER INFORMATION: Synthetic Construct - primer

<400> SEQUENCE: 42
tgatgcggcc ctcgagtcat tggaacgtcg tcactatg              38

<210> SEQ ID NO 43
<211> LENGTH: 45
<212> TYPE: DNA
<213> ORGANISM: Artificial Sequence
<220> FEATURE:
<223> OTHER INFORMATION: Synthetic Construct - primer

<400> SEQUENCE: 43
ataaacaaac aaaccgcgga aaatgtctcg cgaatacttt ccagg        45

<210> SEQ ID NO 44
<211> LENGTH: 40
<212> TYPE: DNA
<213> ORGANISM: Artificial Sequence
<220> FEATURE:
<223> OTHER INFORMATION: Synthetic Construct - primer

<400> SEQUENCE: 44
tgatgcggcc ctcgagtcac tggtacattg ttacgattag            40

<210> SEQ ID NO 45
<211> LENGTH: 1320
<212> TYPE: DNA
<213> ORGANISM: Artificial
<220> FEATURE:
<223> OTHER INFORMATION: Synthetic Construct - Modified DNA

<400> SEQUENCE: 45
atgtctcaaa ttttttaagga tatcccagtt attaaatatg aaggtccagc ttccaagaat        60
cctttgagtt tcaaatacta cgatgcaaac aaggttattg atggtaaacc aatgaaggaa       120
catttgagat acgcaatggc ttggtggcat aatttgtgtg ctaccggtca agatatgttt       180
ggtcctggta ctgcagataa atccttcggt agtaagacag ttggtaccat ggaacatgca       240
catgctaaag ttgatgctgg ttttgaattc atgtccaagt gggtgttga atacttctgt        300
ttccatgatg ctgatttggt tccagaagca gatactttga gtgaaacaaa caaaagattg       360
gatgaaatcg ctgaacatat cgttgctaag caaaaggcaa ctggtattaa atgtttgtgg       420
ggtacagcaa atttgttttc taaccctaga ttcttaaatg gttctggttc ttcaaactca       480
gctgatgttt atgcatacgc tgcagctcaa attaaaaagg ctttggattt gactgttaaa       540
tttggtggtg ttggttatgt tttctggggt ggtagagaag gttacgaaac cttgttgaac       600
actgatgtta agttcgaaca agaaaacatc gctaacttga tgcatttggc agttacttac       660
ggtagatcaa tcggttttaa aggtgacttc tacattgaac caaaacctaa ggaaccaaca       720
aagcatcaat atgattttga tgcagctact acaattggtt tcattagaca atacggtttg       780
gaaaaggatt tcaagttgaa catcgaagca aaccatgcta cattagcagg tcataccttc       840

```
caacatgatt tgagaatctc tgctattaat ggcatgttag gttcagttga tgcaaacaca      900
ggtgacccat tgttaggttg ggataccgat gaatttcctt attccgttta cgataccact      960
ttggctatgt acgaaattat taaggcaggt ggtttgaccg gtggtttgaa ttttgattcc     1020
aaggttagaa gaccaagtta cacacatgaa gatttgtttt acggtttcat ttgggtatg     1080 gattctttcg ctttgggttt gattaaagca aaggctttga ttgcagatgg tagattggat     1140
tcattcgtta aggatagata cgcttcttac ggttcaggta ttggtgctaa gattagagat     1200
cattctgcaa ctttggaaga attagcagct tatgcattag ctaaagatac agttgctttg     1260
cctggttccg gtagacaaga atacttagaa agtattatta ccaaatttt gtttcaataa      1320
```

<210> SEQ ID NO 46
<211> LENGTH: 1314
<212> TYPE: DNA
<213> ORGANISM: Artificial
<220> FEATURE:
<223> OTHER INFORMATION: Synthetic Construct - Modified DNA

<400> SEQUENCE: 46

```
atggctaagg aatacttccc acaaatccaa aagattaaat tcgagggtaa agattctaaa       60
aatcctttgg cattccatta ctacgatgct gaaaaggaag ttatgggtaa aaagatgaag      120
gattggttga gattcgctat ggcatggtgg catactttgt gtgcagaagg tgctgatcaa      180
tttggtggtg gtactaagtc attcccatgg aacgaaggta cagatgcaat cgaaatcgct      240
aagcaaaagg ttgatgctgg tttcgaaatc atgcaaaagt tgggtatccc ttactactgt      300
ttccatgatg ttgatttggt ttccgagggt aacagtatcg aagaatacga atccaacttg      360
aaagcagttg ttgcttactt aaaggaaaag caaaaggaaa caggtattaa gttgttgtgg      420
tccaccgcaa acgttttcgg tcataagaga tacatgaacg gtgctagtac taacccagat      480
ttcgatgttg ttgctagagc aatcgttcaa attaaaaatg caatcgatgc tggtattgaa      540
ttgggtgcag aaaactatgt tttctggggt ggtagagaag gttacatgtc tttgttgaac      600
acagatcaaa agagagaaaa agaacatatg gctaccatgt taactatggc aagagattat      660
gctagatcaa agggttttaa aggtaccttc ttgattgaac aaagcctat ggaaccaact      720 aaacatcaat acgatgttga tactgaaaca gcaattggtt tcttgaaggc tcataatttg      780
gataaggatt tcaaggttaa catcgaagtt aaccatgcaa ctttggctgg tcatacattt     840
gaacatgaat tagcttgtgc agttgatgca ggcatgttgg gttctattga tgctaatcgt      900
ggtgactatc aaaacggttg ggatactgat caattcccta tcgatcaata cgaattagtt      960
caagcttgga tggaaatcat cagaggtggt ggttttgtta caggtggtac caatttcgat     1020
gcaaaaacca aagaaactc tactgatttg gaagatatca tcatcgctca tgtttctggt     1080
atggatgcta tggcaagagc tttggaaaat gctgcaaagt tgttacaaga atccccatac     1140
acaaagatga aaaggaaag atacgcttct ttcgattcag gtatcggtaa agatttcgaa     1200
gatggtaaat tgacattaga acaagtttac gaatacggta aaagaacgg tgaacctaag     1260 caaaccagtg gtaaacaaga attgtatgaa gcaattgttg ctatgtacca ataa          1314
```

<210> SEQ ID NO 47
<211> LENGTH: 1317
<212> TYPE: DNA
<213> ORGANISM: Artificial
<220> FEATURE:
<223> OTHER INFORMATION: Synthetic Construct - Modified DNA

<400> SEQUENCE: 47

```
atgaagaatt acttcccaaa tgtcccagaa gtgaaatatg aaggccccaa ttcaaccaac      60
ccatttgcat tcaaatacta cgacgcaaac aaggttgttg caggaaaaac tatgaaagag     120
cactgtaggt ttgcacttag ctggtggcat actttatgcg caggtggagc tgacccgttc     180
ggagttacta ctatggacag aacgtacggt aacattactg acccaatgga actagcaaaa     240
gcaaaagttg acgcaggttt tgaactgatg accaagcttg gtattgaatt ttttttgtttt    300
catgacgctg atattgcccc agaaggtgac acgttcgaag aatccaaaaa aaatctatttt    360
gaaattgtag attatataaa ggaaaaaatg gatcaaacag gaatcaaaact actttggggt    420
actgccaata attttctca tccccgtttt atgcacggcg catccacatc ttgtaacgct      480
gacgtgttcg cgtacgccgc tgcaaagatc aaaaacgcgt tggatgccac tataaaattg     540
ggtggtaaag gttacgtctt ctgggggggt agggaaggtt acgagacctt gcttaacact     600
gatctgggtt tggaattaga caatatggcc agattaatga aatggcagt tgaatacgga     660
agagcaaatg gcttcgatgg cgattttat atagagccca aacctaaaga gcctactaaa     720
catcaatatg actttgacac cgcgactgtc ttagccttttt taagaaagta cgggcttgaa   780
aaagacttca aaatgaatat cgaagccaac catgcgacgt ggctggtca taccttttgag   840
catgagctag ccatggcaag agtcaatggc gcctttgggt ctgtcgatgc taatcagggc    900
gatcctaacc ttggatggga tacgatcaa tttcctacag atgttcactc agcaacactt     960
gcaatgttgg aagttctgaa agctggaggc tttactaatg gtggtctaaa ctttgatgct  1020
aaggttagaa gaggcagttt cgaatttgac gacatcgcat acggttatat tgctggtatg  1080
gacacgttcg ctttaggcct gattaaagcc gctgaaatta ttgatgatgg cagaatagct  1140
aagtttgttg atgacagata cgcaagttac aaaaccggta ttggtaaggc catcgtagac  1200
gggactacta gcttggaaga acttgaacag tatgttttga ctcattccga accagtaatg  1260
caatctggta gacaagaagt cttggagact attgtcaata acatcttgtt tagatga      1317
```

<210> SEQ ID NO 48
<211> LENGTH: 48
<212> TYPE: DNA
<213> ORGANISM: Artificial
<220> FEATURE:
<223> OTHER INFORMATION: Synthetic Construct - primer

<400> SEQUENCE: 48

```
ataaacaaac aaaccgcgga aaatgtctca aattttttaag gatatccc                48
```

<210> SEQ ID NO 49
<211> LENGTH: 49
<212> TYPE: DNA
<213> ORGANISM: Artificial
<220> FEATURE:
<223> OTHER INFORMATION: Synthetic Construct - primer

<400> SEQUENCE: 49

```
tgatgcggcc ctcgagttat tgaaacaaaa tttggttaat aatactttc              49
```

<210> SEQ ID NO 50
<211> LENGTH: 41
<212> TYPE: DNA
<213> ORGANISM: Artificial
<220> FEATURE:
<223> OTHER INFORMATION: Synthetic Construct - primer

<400> SEQUENCE: 50

```
ataaacaaac aaaccgcgga aaatggctaa ggaatacttc c                           41

<210> SEQ ID NO 51
<211> LENGTH: 43
<212> TYPE: DNA
<213> ORGANISM: Artificial
<220> FEATURE:
<223> OTHER INFORMATION: Synthetic Construct - primer

<400> SEQUENCE: 51
tgatgcggcc ctcgagttat tggtacatag caacaattgc ttc                        43

<210> SEQ ID NO 52
<211> LENGTH: 48
<212> TYPE: DNA
<213> ORGANISM: Artificial
<220> FEATURE:
<223> OTHER INFORMATION: Synthetic Construct - primer

<400> SEQUENCE: 52
ataaacaaac aaaccgcgga aaatgaagaa ttacttccca aatgtccc                   48

<210> SEQ ID NO 53
<211> LENGTH: 49
<212> TYPE: DNA
<213> ORGANISM: Artificial
<220> FEATURE:
<223> OTHER INFORMATION: Synthetic Construct - primer

<400> SEQUENCE: 53
tgatgcggcc ctcgagtcat ctaaacaaga tgttattgac aatagtctc                  49
```